United States Patent
Watanabe

(10) Patent No.: US 9,940,710 B2
(45) Date of Patent: Apr. 10, 2018

(54) BIOLOGICAL INFORMATION DETECTION DEVICE EQUIPPED WITH LIGHT SOURCE PROJECTING AT LEAST ONE DOT ONTO LIVING BODY

(71) Applicant: Panasonic Intellectual Property Management Co., Ltd., Osaka (JP)

(72) Inventor: Hisashi Watanabe, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 126 days.

(21) Appl. No.: 15/169,770

(22) Filed: Jun. 1, 2016

(65) Prior Publication Data

US 2016/0358332 A1    Dec. 8, 2016

(30) Foreign Application Priority Data

Jun. 4, 2015    (JP) ................................. 2015-113898

(51) Int. Cl.
*G06T 7/00* (2017.01)
*H04N 5/225* (2006.01)
(Continued)

(52) U.S. Cl.
CPC .......... *G06T 7/0012* (2013.01); *A61B 5/0033* (2013.01); *A61B 5/021* (2013.01);
(Continued)

(58) Field of Classification Search
CPC .... G06T 7/0012; H04N 5/2256; H04N 5/332; H04N 9/3176; A61B 5/0261; A61B 5/021;
(Continued)

(56) References Cited

U.S. PATENT DOCUMENTS 6,859,658 B1    2/2005   Krug
7,039,446 B2 *  5/2006   Ruchti ................. A61B 5/0071
                                                    600/310
(Continued)

FOREIGN PATENT DOCUMENTS

JP          6-054836       3/1994
JP       2002-200050       7/2002
(Continued)

OTHER PUBLICATIONS

Tsutomu Kuroda et al., "Analysis of facial color and skin temperature in emotional change and its synthesis of facial color", Human Interface Society, vol. 1 No. 1, pp. 15-20, 1999.

*Primary Examiner* — Neil Mikeska
(74) *Attorney, Agent, or Firm* — McDermott Will & Emery LLP

(57) ABSTRACT

A biological information detection device includes first and second light sources, an image capturing system, and an arithmetic circuit. The first and second light sources project, onto a living body, at least one first dot formed by first light and at least one second dot formed by second light, respectively. The image capturing system includes first photodetector cells and second photodetector cells. The image capturing system generates and outputs a first image signal and a second image signal. The arithmetic circuit generates information concerning the living body, by using the first and second image signals. The first light includes fifth light. The second light includes sixth light. Each of the fifth light and the sixth light has a wavelength in a range from 650 nm to 950 nm. The wavelength of the sixth light is longer than that of the fifth light by 50 nm or more.

13 Claims, 26 Drawing Sheets

(51) Int. Cl.
*H04N 5/33* (2006.01)
*A61B 5/026* (2006.01)
*A61B 5/021* (2006.01)
*A61B 5/00* (2006.01)
*G06K 9/00* (2006.01)
*A61B 5/024* (2006.01)
*A61B 5/16* (2006.01)
*H04N 9/31* (2006.01)

(52) U.S. Cl.
CPC ........ *A61B 5/0261* (2013.01); *A61B 5/02416* (2013.01); *A61B 5/165* (2013.01); *A61B 5/725* (2013.01); *G06K 9/00255* (2013.01); *G06K 9/00906* (2013.01); *H04N 5/2256* (2013.01); *H04N 5/332* (2013.01); *H04N 9/3176* (2013.01); *A61B 5/02116* (2013.01); *A61B 2576/00* (2013.01); *G06T 2207/30104* (2013.01); *G06T 2207/30201* (2013.01); *H04N 2209/047* (2013.01)

(58) Field of Classification Search
CPC ... A61B 5/725; A61B 5/0033; A61B 5/02416; A61B 5/165; G06K 9/00255; G06K 9/00906
See application file for complete search history.

(56) References Cited

U.S. PATENT DOCUMENTS

| | | | |
|---|---|---|---|
| 2013/0148326 A1* | 6/2013 | Goldfain | G01J 3/0224 362/19 |
| 2013/0231572 A1* | 9/2013 | Konishi | A61B 5/153 600/473 |
| 2013/0329031 A1 | 12/2013 | Miura et al. | |
| 2014/0294251 A1* | 10/2014 | Jo | G06K 9/00885 382/115 |
| 2014/0303454 A1 | 10/2014 | Clifton et al. | |

FOREIGN PATENT DOCUMENTS

| | | |
|---|---|---|
| JP | 2003-517342 | 5/2003 |
| JP | 2005-052385 | 3/2005 |
| JP | 2005-218507 | 8/2005 |
| JP | 2008-237244 | 10/2008 |
| JP | 2008-302260 | 12/2008 |
| JP | 2010-124935 | 6/2010 |
| JP | 2014-526549 | 10/2014 |
| JP | 2014-527863 | 10/2014 |
| WO | 2012/143977 | 10/2012 |
| WO | 2013/042006 | 3/2013 |

* cited by examiner

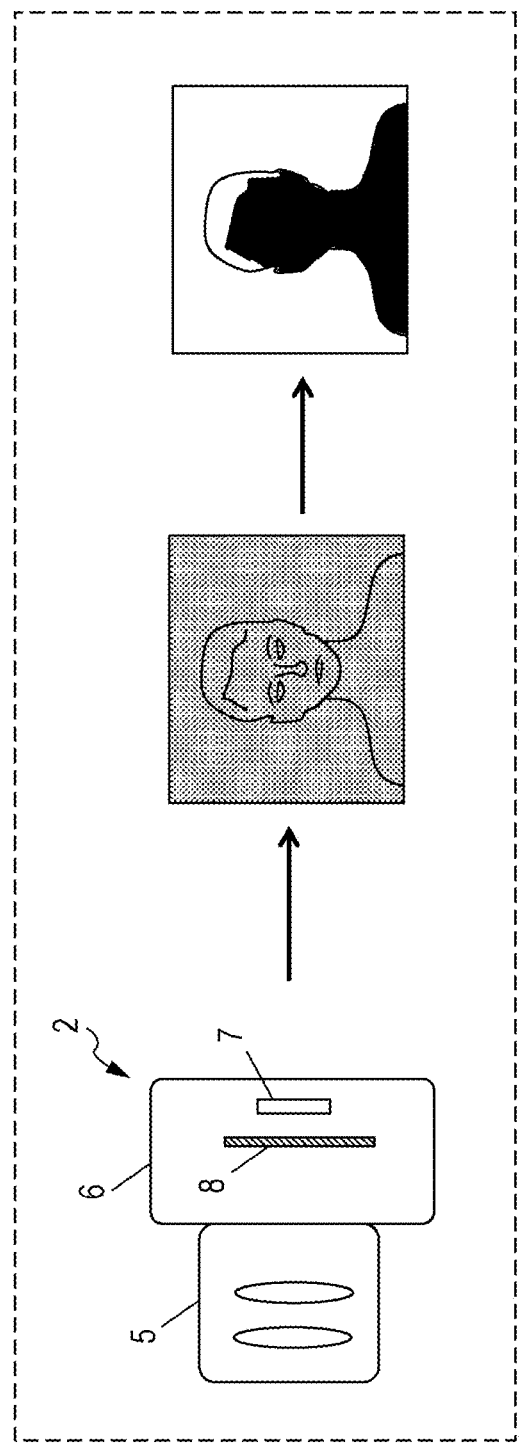

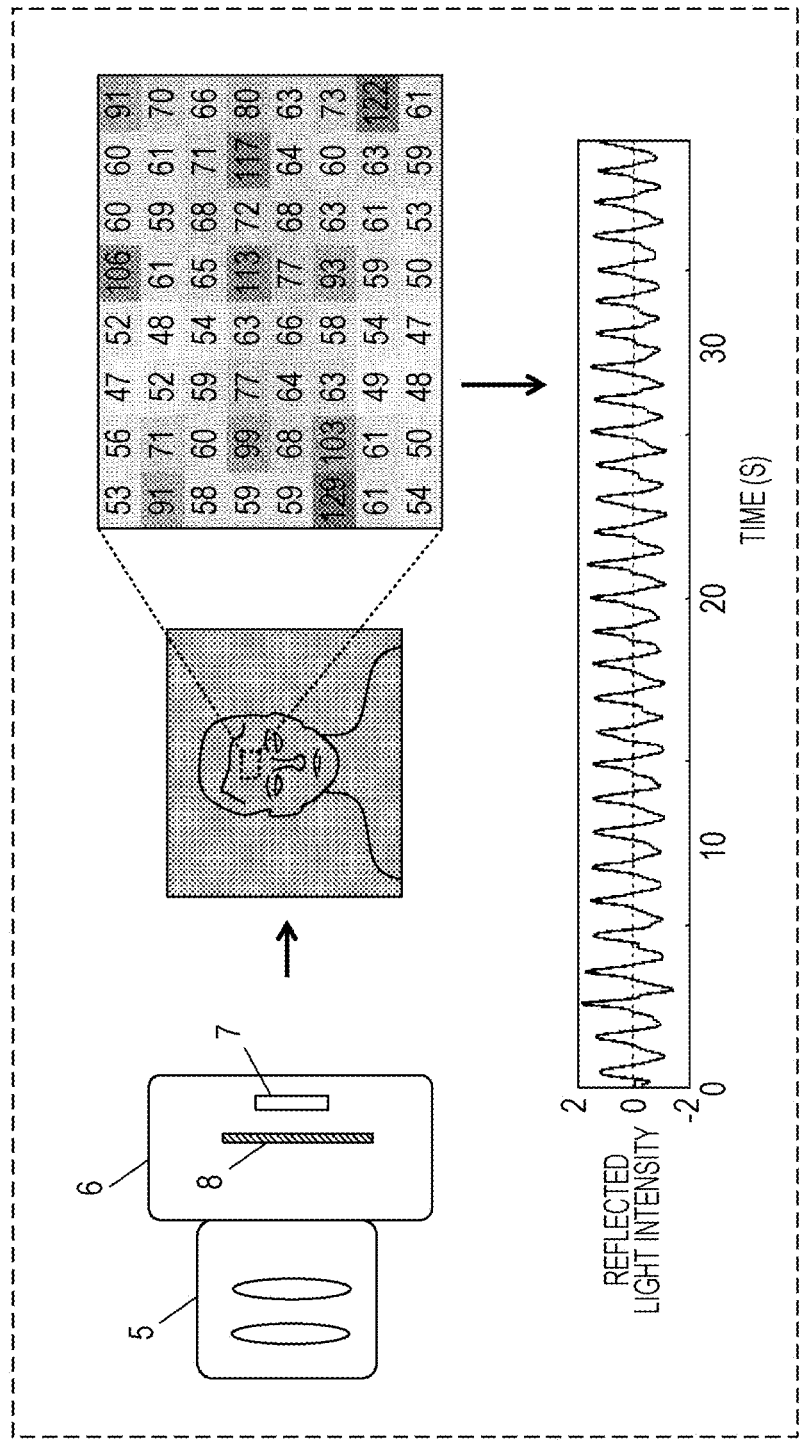

BIOLOGICAL INFORMATION DETECTION DEVICE EQUIPPED WITH LIGHT SOURCE PROJECTING AT LEAST ONE DOT ONTO LIVING BODY

BACKGROUND

1. Technical Field

The present disclosure relates to biological information detection devices and, more particularly, to a biological information detection device, a biological information detection method, and a psychological change detection method for detecting biological information, such as heartbeat, in a non-contact manner.

2. Description of the Related Art

Heartbeat, blood flow, blood pressure, and blood oxygen saturation are widely used as basic parameters for determining the health condition of a person. These pieces of biological information relating to blood are typically measured by contact-type measuring instruments. Since contact-type measuring instruments are attached to the body of a subject, measurement, especially, long continuous measurement, sometimes incurs the subject's discomfort.

Various attempts have been made to easily measure basic biological information for determining the health condition of a person. For example, Japanese Unexamined Patent Application Publication No. 2005-218507 discloses a method for detecting heart rate in a non-contact manner on the basis of image information of a face or the like obtained with a camera. Japanese Unexamined Patent Application Publication (Translation of PCT Application) No. 2003-517342 discloses a method for measuring, using a white light source and a laser light source, blood oxygen saturation on the basis of a laser Doppler effect of laser light scattered behind the surface of a living body. Japanese Unexamined Patent Application Publication (Translation of PCT Application) No. 2014-527863 discloses a method for measuring, using an ordinary color camera, blood oxygen saturation while removing the influence of ambient light.

In addition, many methods for estimating a psychological change of a person have been proposed. For example, Japanese Unexamined Patent Application Publication Nos. 6-54836 and 2008-237244 disclose methods for detecting, with thermography, a decrease in temperature at a nose portion that occurs when a person feels stress (nervous) or concentrates.

SUMMARY

In one general aspect, the techniques disclosed here feature a biological information detection device including: a first light source that, in operation, projects, onto a living body, at least one first dot formed by first light; a second light source that, in operation, projects, onto the living body, at least one second dot formed by second light; an image capturing system including first photodetector cells that, in operation, detect third light from the living body on which the at least one first dot is projected, and second photodetector cells that, in operation, detect fourth light from the living body on which the at least one second dot is projected, the image capturing system, in operation, generating and outputting a first image signal and a second image signal, the first image signal denoting a first image of the living body on which the at least one first dot is projected, the second image signal denoting a second image of the living body on which the at least one second dot is projected; and an arithmetic circuit that, in operation, generates information concerning the living body by using the first image signal and the second image signal output from the image capturing system and outputs the generated information, wherein: the first light includes fifth light having a wavelength longer than or equal to 650 nm and shorter than or equal to 950 nm; the second light includes sixth light having a wavelength longer than or equal to 650 nm and shorter than or equal to 950 nm; and the wavelength of the sixth light is longer than the wavelength of the fifth light by 50 nm or more.

It should be noted that general or specific embodiments may be implemented as an element, a device, a system, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3B is a diagram illustrating an example of a configuration of a camera and an example of an output image in accordance with the first embodiment;

FIG. 6A is a diagram illustrating an example of a configuration and an example of biological information (heart rate) generated in accordance with a second embodiment;

DETAILED DESCRIPTION

Figure 1A:
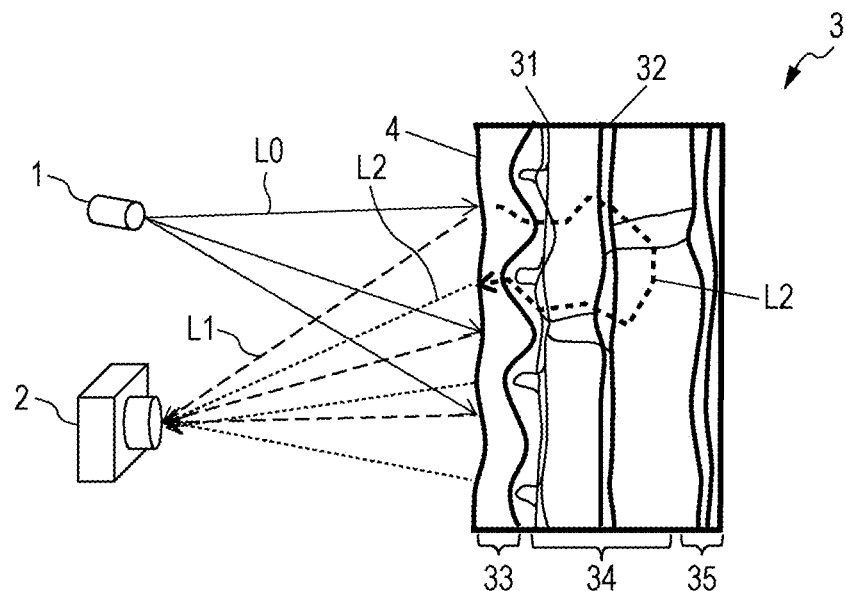
FIG. 1A is a diagram for explaining a basic concept of how biological information is obtained in an embodiment of the present disclosure.

Underlying Knowledge Forming Basis of the Present Disclosure

Prior to description of embodiments of the present disclosure, underlying knowledge forming the basis of the present disclosure will be described.

As described above, various attempts have been made to measure basic biological information for determining the health condition of a person. For example, a method for detecting heart rate in a non-contact manner on the basis of image information of a face or the like obtained with a camera has been proposed in Japanese Unexamined Patent Application Publication No. 2005-218507. In the method according to Japanese Unexamined Patent Application Publication No. 2005-218507, heart rate is determined by analyzing a spatial frequency component of an obtained color image. However, since the accuracy achieved by this method decreases due to the influence of disturbance light, such as light illuminating a room, stable detection is difficult.

Pulse oximeters are commonly used to measure blood oxygen saturation. Pulse oximeters radiate two wavelengths of light in a red to near-infrared wavelength range onto a finger inserted therein and measure transmittance of the light. In this way, pulse oximeters are able determine a ratio between an oxyhemoglobin concentration and a deoxyhemoglobin concentration in blood. Pulse oximeters are capable of measuring blood oxygen saturation with a simple configuration. However, since pulse oximeters are contact-type devices, they may make people feel restrained.

Japanese Unexamined Patent Application Publication (Translation of PCT Application) No. 2003-517342 discloses an example of a non-contact-type blood oxygen saturation measuring device. This device measures, using a white light source and a laser light source, blood oxygen saturation on the basis of a laser Doppler effect of laser light scattered behind the surface of a living body. This method, however, makes a configuration of the device complicated, and the resulting signal is weak.

In Japanese Unexamined Patent Application Publication (Translation of PCT Application) No. 2014-527863, a method for measuring, using an ordinary color camera, blood oxygen saturation while removing the influence of ambient light has been proposed. Since this method is greatly influenced by reflected light reflected by the surface of skin, it is difficult to measure blood oxygen saturation stably at a high accuracy.

As described above, non-contact-type blood oxygen saturation measuring methods of the related art have issues related to the accuracy and the stability. There is substantially no non-contact-type blood oxygen saturation measuring device that is put into practical use at present.

On the other hand, many methods for estimating, using thermography, a psychological change of a person have been proposed (for example, Japanese Unexamined Patent Application Publication Nos. 6-54836 and 2008-237244). In these methods, a decrease in temperature at a nose portion is detected with thermography. Since lots of arteriovenous anastomosis is located at the nose portion of a person, blood circulation is easily disturbed by the influence of the autonomic nervous system. A psychological change, such as stress or nervousness, influences the autonomic nervous system. The influenced autonomic nervous system causes a decrease in blood flow at the nose portion, which then causes a decrease in temperature at the nose portion. The devices disclosed in Japanese Unexamined Patent Application Publication Nos. 6-54836 and 2008-237244 detect such a change in temperature with thermography, thereby estimating a psychological change of the subject.

Methods using thermography have a low responsivity because it takes time for temperature to decrease and are influenced by environmental temperature. It is considered that a psychological change estimating method that has a high responsivity and is more resistant to the influence of environmental temperature can be established if blood flow at the surface of the face can be accurately measured. However, no reliable method for measuring blood flow under skin at a high accuracy in a non-contact manner is established at present. Thus, methods having the above-described issues and using an expensive device such as thermography are predominant.

The inventor has focused on the above-described issues and has studied a configuration for addressing the issues. The inventor consequently has found out that the issues can be addressed by obtaining an image using a light source that projects at least one dot onto the surface of a living body and by separating, through signal processing, a component relating to directly reflected light in the image from a component relating to diffused light caused in the living body. A biological information detection device according to an aspect of the present disclosure includes at least one light source that, in operation, projects at least one dot formed by light onto a target including a living body, an image capturing system that includes photodetector cells and that, in operation, generates and outputs an image signal denoting an image of the target on which the at least one dot is projected, and an arithmetic circuit that is connected to the image capturing system and, in operation, processes the image signal output from the image capturing system. The arithmetic circuit may, in operation, generate and output information concerning the living body by using the image signal. Such a configuration allows biological information to be obtained at a high accuracy.

Principle

A principle allowing a biological information detection device to obtain biological information at a high accuracy will be described below.

FIG. 1A is a diagram illustrating a schematic configuration of a biological information detection device according to an illustrative embodiment of the present disclosure. The biological information detection device includes a light source 1 and a camera 2, which is an image capturing system. The light source 1 is an array point light source that projects a plurality of discretely arranged points (also referred to as "arrayed points" or "dot pattern" herein) onto a target including a living body 3. The light source 1 is arranged such that a plurality of points are projected onto the living body 3. The camera 2 includes an image sensor, captures an image of a living-body surface 4, and generates and outputs an image signal.

Figure 1B:
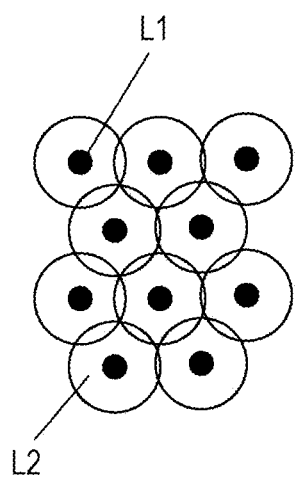
FIG. 1B is a diagram for explaining characteristics of an image of the surface of a living body, obtained with a camera.

FIG. 1B is a diagram for explaining characteristics of the image of the living-body surface 4, obtained by the camera 2. Outgoing light LO from the light source 1 is reflected by the living-body surface 4. Surface reflected light L1 reflected by the living-body surface 4 maintains an image of the arrayed points formed by the light source 1. In contrast, inside-body scattered light L2 that exits from the living-body surface 4 after entering the living body 3 and being scattered inside the living body 3 no longer maintains the image of the arrayed points formed by the light source 1 because of strong scattering caused inside the living body 3. The use of the light source 1 allows the surface reflected light L1 and the inside-body scattered light L2 to be spatially separated from each other easily.

The living body 3 illustrated in FIG. 1A represents human skin and includes epidermis 33, dermis 34, and a subcutaneous tissue 35. No blood vessel is located at the epidermis 33, whereas a capillary 31 and an arteriole/venule 32 are located at the dermis 34. Since there is no blood vessel at the epidermis 33, the surface reflected light L1 does not contain information relating to blood (hereinafter, referred to as blood-related information). Since the epidermis 33 includes melanin that strongly absorbs light, the surface reflected light L1 reflected by the epidermis 33 becomes noise when blood-related information is obtained. Thus, the surface reflected light L1 is not only useless to obtain blood-related information but also disturbs acquisition of accurate blood-related information. Biological information can be detected at a high accuracy by suppressing the influence of the surface reflected light and by efficiently obtaining information of the inside-body scattered light.

To address the issues described above, embodiments of the present disclosure has a novel configuration with which directly reflected light and inside-body scattered light are spatially separated using an array point light source and an image capturing system. With this novel configuration, information concerning the living body can be measured at a high accuracy in a non-contact manner.

In the related art, methods using polarizing illumination such as the one disclosed in Japanese Unexamined Patent Application Publication No. 2002-200050 have been used to separate directly reflected light reflected by the living-body surface. In such methods using polarizing illumination, a polarizer having a polarized light transmission axis perpendicular to a polarization direction of illumination light reflected by an image-capturing target is used. The influence of surface reflected light can be suppressed by capturing an image with a camera through such a polarizer. However, since the degree of polarization of surface reflected light reflected by an uneven surface such as skin changes depending on the position, separation of such directly reflected light is not sufficient. With a method according to an aspect of the present disclosure, the influence of surface reflected light can be effectively suppressed since directly reflected light and scattered light is successfully spatially separated.

In the biological information detection device according to an embodiment of the present disclosure, the wavelength of light emitted by the light source can be set to be, for example, longer than or equal to approximately 650 nm and shorter than or equal to approximately 950 nm. This wavelength range is within a wavelength range of red to near-infrared light. Herein, the term "light" is used not only for visible light but also for infrared. The above wavelength range is called "optical tissue window" and is known as a range in which absorbance in the body is low.

Figure 2:
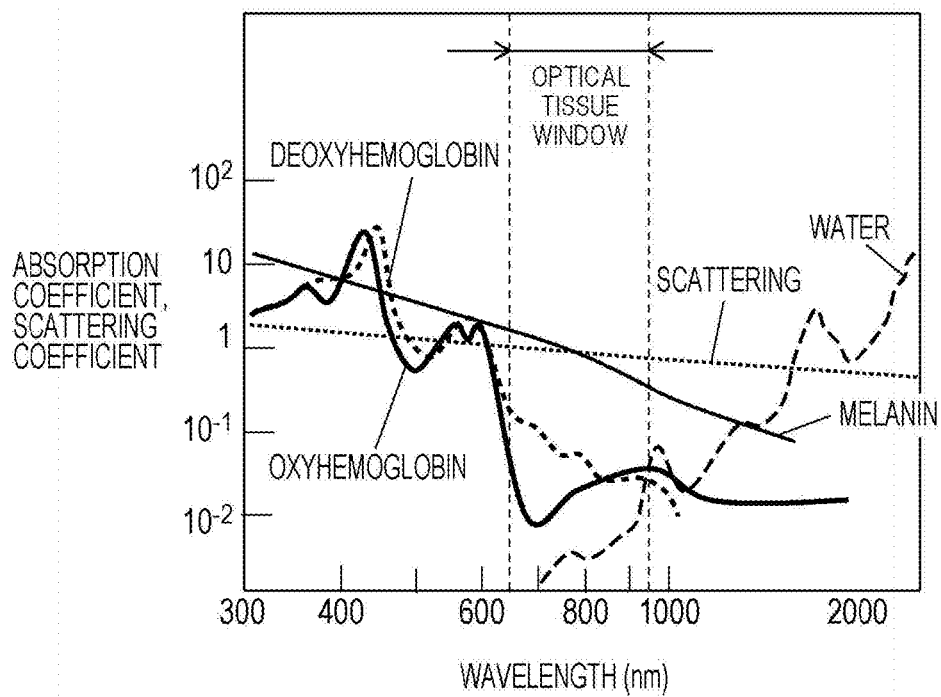
FIG. 2 is a diagram illustrating an absorption coefficient and a scattering coefficient of hemoglobin, melanin, and water, which are main components of a living body, in a wavelength range from visible light to near-infrared light.

FIG. 2 is a diagram illustrating wavelength dependency of a light absorption coefficient and an inside-body light scattering coefficient for oxyhemoglobin, deoxyhemoglobin, melanin, and water. Light is absorbed mainly by blood (i.e. hemoglobin) in a visible light range of 650 nm or shorter, whereas light is absorbed mainly by water in a wavelength range longer than 950 nm. Therefore, light in these wavelength ranges is not suitable for obtaining biological information. In contrast, in a wavelength range from approximately 650 nm to approximately 950 nm, the absorption coefficients for hemoglobin and water are relatively low, and the scattering coefficient is relatively high. Therefore, light of this wavelength range returns to the body surface after entering the body and being strongly scattered. Accordingly, with light of this wavelength range, biological information can be efficiently obtained.

A biological information detection device according to an embodiment of the present disclosure mainly utilizes light of this wavelength range corresponding to the "optical tissue window". With this configuration, since the biological information detection device is able to separate and detect light directly reflected by the living-body surface and returning light that has been scattered inside the living body, it can efficiently obtain biological information.

The present disclosure includes, for example, aspects recited in the following items.

[Item 1] A biological information detection device includes:

a first light source that, in operation, projects, onto a living body, at least one first dot formed by first light;

a second light source that, in operation, projects, onto the living body, at least one second dot formed by second light;

an image capturing system including first photodetector cells that, in operation, detect third light from the living body on which the at least one first dot is projected, and second photodetector cells that, in operation, detect fourth light from the living body on which the at least one second dot is projected, the image capturing system, in operation, generating and outputting a first image signal and a second image signal, the first image signal denoting a first image of the living body on which the at least one first dot is projected, the second image signal denoting a second image of the living body on which the at least one second dot is projected; and an arithmetic circuit that, in operation, generates information concerning the living body by using the first image signal and the second image signal output from the image capturing system and outputs the generated information, wherein:

the first light includes fifth light having a wavelength longer than or equal to 650 nm and shorter than or equal to 950 nm;

the second light includes sixth light having a wavelength longer than or equal to 650 nm and shorter than or equal to 950 nm; and the wavelength of the sixth light is longer than the wavelength of the fifth light by 50 nm or more.

In the biological information detection device according to Item 1, the at least one first dot may comprise first dots formed by the first light.

In the biological information detection device according to Item 1, the at least one second dot may comprise second dots formed by the second light.

In the biological information detection device according to Item 1, the at least one first dot may comprise first dots formed by the first light, and the first dots may be arranged in a line.

In the biological information detection device according to Item 1, the at least one second dot may comprise second dots formed by the second light, and the econd dots may be arranged in a line.

In the biological information detection device according to Item 1, the at least one first dot may comprise first dots formed by the first light, and the first dots may be arranged in an array.

In the biological information detection device according to Item 1, the at least one second dot may comprise second dots formed by the second light, and the second dots may be arranged in an array.

[Item 2] In the biological information detection device according to Item 1, the image capturing system may further include an image sensor having an imaging surface divided into a first region in which the first photodetector cells are disposed and a second region in which the second photodetector cells are disposed, a first optical system that, in operation, forms the first image at the first region, and a second optical system that, in operation, forms the second image at the second region.

[Item 3] In the biological information detection device according to Item 2, the image capturing system may further include a first bandpass filter that is disposed on a path of the third light entering the first region and that, in operation, passes the third light, and a second bandpass filter that is disposed on a path of the fourth light entering the second region and that, in operation, passes the fourth light.

[Item 4] In the biological information detection device according to Item 1, the image capturing system may further include an image sensor having an imaging surface at which the first photodetector cells and the second photodetector cells are disposed, and including first bandpass filters that face the first photodetector cells and, in operation, pass the third light and second bandpass filters that face the second photodetector cells and, in operation, pass the fourth light, and an optical system that forms the first image and the second image on the imaging surface.

[Item 5] In the biological information detection system according to Item 1, the image capturing system may further include an image sensor having an imaging surface at which the first photodetector cells, the second photodetector cells, and third photodetector cells are disposed, and including first bandpass filters that face the first photodetector cells and, in operation, pass the third light, second bandpass filters that face the second photodetector cells and pass the fourth light, and third bandpass filters that face the third photodetector cells and, in operation, pass visible light, and an optical system that, in operation, forms the first image and the second image on the imaging surface, wherein:

the third bandpass filters include color filters having different transmission wavelength ranges; and the image sensor generates and outputs a color image signal by using the third photodetector cells.

[Item 6] In the biological information detection device according to any one of Items 1 to 5, the arithmetic circuit may, in operation, generate information indicating a blood oxygen saturation of the living body by using the first image signal and the second image signal and output the generated information.

[Item 7] In the biological information detection device according to any one of Items 1 to 5, the arithmetic circuit may, in operation, calculate, based on the first image signal and the second image signal, a blood flow and a blood oxygen saturation of the living body, generate, based on the blood flow and the blood oxygen saturation, information indicating at least one item selected from the group consisting of a physical condition, an emotion, and a concentration degree of the living body, and output the generated information.

[Item 8] In the biological information detection device according to any one of Items 1 to 5, when the first image and the second image include at least one portion selected from the group consisting of a forehead portion and a nose portion of the living body, the arithmetic circuit may, in operation, calculate, based on the first image signal and the second image signal, a blood flow and a blood oxygen saturation at the at least one portion selected from the group consisting of the forehead portion and the nose portion, generate, based on a change in the blood flow over time and a change in the blood oxygen saturation over time, information indicating at least one item selected from the group consisting of a physical condition, an emotion, and a concentration degree of the living body, and output the generated information.

[Item 9] In the biological information detection device according to any one of Items 1 to 5, when the first image and the second image include a forehead portion and a nose portion of the living body,
the arithmetic circuit may, in operation,
calculate, based on the first image signal and the second image signal, a blood flow and a blood oxygen saturation at the forehead portion and a blood flow and a blood oxygen saturation at the nose portion,
generate, based on comparison of a change in the blood flow over time and a change in the blood oxygen saturation over time at the forehead portion with a change in the blood flow over time and a change in the blood oxygen saturation over time at the nose portion, information indicating at least one item selected from the group consisting of a physical condition, an emotion, and a concentration degree of the living body, and
output the generated information.

[Item 10] In the biological information detection device according to any one of Items 1 to 9, each of the first light source and the second light source may be a laser light source.
In the biological information detection device according to Item 10, the laser light source may project a random dot pattern.

[Item 11] In the biological information detection device according to Item 1, the image capturing system may further include
an image sensor having an imaging surface at which the first photodetector cells and the second photodetector cells are disposed,
an optical system that, in operation, forms the first image and the second image on the imaging surface, and
an adjusting mechanism that, in operation, adjusts focus of the optical system, and
wherein the adjusting mechanism adjusts the focus to maximize contrast of the first image and the second image.

[Item 12] In the biological information detection device according to any one of Items 1 to 11, the arithmetic circuit may, in operation, perform a face recognition process by using the first image signal and the second image signal, and
generate the information concerning the living body in a case where the first image and the second image include at least one portion selected from the group consisting of a forehead, a nose, a mouth, an eyebrow, and hair of the living body.

[Item 13] In the biological information detection device according to any one of Items 1 to 5, the information concerning the living body may be information concerning at least one item selected from the group consisting of a melanin concentration, presence or absence of a spot, and presence or absence of a bruise.

[Item 14] A biological information detection device includes
at least one light source that projects, onto a target, a dot pattern formed by light, the target including a living body;
an image capturing system, including photodetector cells, that generates and outputs an image signal denoting an image of the target on which the dot pattern is projected; and
an arithmetic circuit that is connected to the image capturing system and that generates and outputs information concerning the living body by using the image signal output from the image capturing system.

[Item 15] In the biological information detection device according to Item 14, the light may include light of a wavelength longer than or equal to 650 nm and shorter than or equal to 950 nm.

[Item 16] In the biological information detection device according to Item 14 or 15, the information concerning the living body may include information concerning at least one selected from the group consisting of a position of the living body in the image, a heart rate of the living body, a blood flow of the living body, and a blood oxygen saturation of the living body.

[Item 17] In the biological information detection device according to any one of Items 14 to 16, the image capturing system may further include
a bandpass filter that passes light of a wavelength range including at least part of a wavelength range of the light emitted by the light source, and
an image capturing element having an imaging surface at which the photodetector cells are disposed and arranged such that the light that has passed the bandpass filter enters the imaging surface.

[Item 18] In the biological information detection device according to any one of Items 14 to 17, the arithmetic circuit may determine, based on a ratio between a standard deviation and an average of pixel values of a specific pixel included in the image and pixels neighboring the specific pixel, whether the living body is located at a position corresponding to the specific pixel and may output information indicating whether the living body is located at the position.

[Item 19] In the biological information detection device according to any one of Items 14 to 18, the arithmetic circuit may generate and output information concerning at least one selected from the group consisting of a heart rate, a blood pressure, and a blood flow of the living body, based on a change in a signal in time, the signal being obtained by performing a low-pass filtering process on at least part of the image signal.

Embodiments of the present disclosure will be described in more detail below. The following embodiments relate mainly to a biological information detection device that measures biological information in a non-contact manner, assuming that a face of a person is a living-body surface. Note that techniques of the embodiments of the present disclosure are applicable not only to a face of a person but also to portions other than the face of a person or to skin of animals other than human.

First Embodiment

A system in which a technique of the present disclosure is applied to human detection will be described as a first embodiment. Development relating to human detection is underway for the purpose of detecting disaster victims buried under rubble or the like at a disaster site, for example. Finding disaster victims within 72 hours from occurrence of a disaster is critical in terms of the survival rate of disaster victims. Accordingly, a simple and stable human detection system is needed. The human detection technology is also utilized in fields of security and transportation. The human detection technology plays an important role to find an intruder in the field of security and to detect foot passengers in the field of transportation. There is also an increasing need for a system capable of selectively detecting a living body (especially, human body) in an image including various constructions or objects.

Figure 3A:
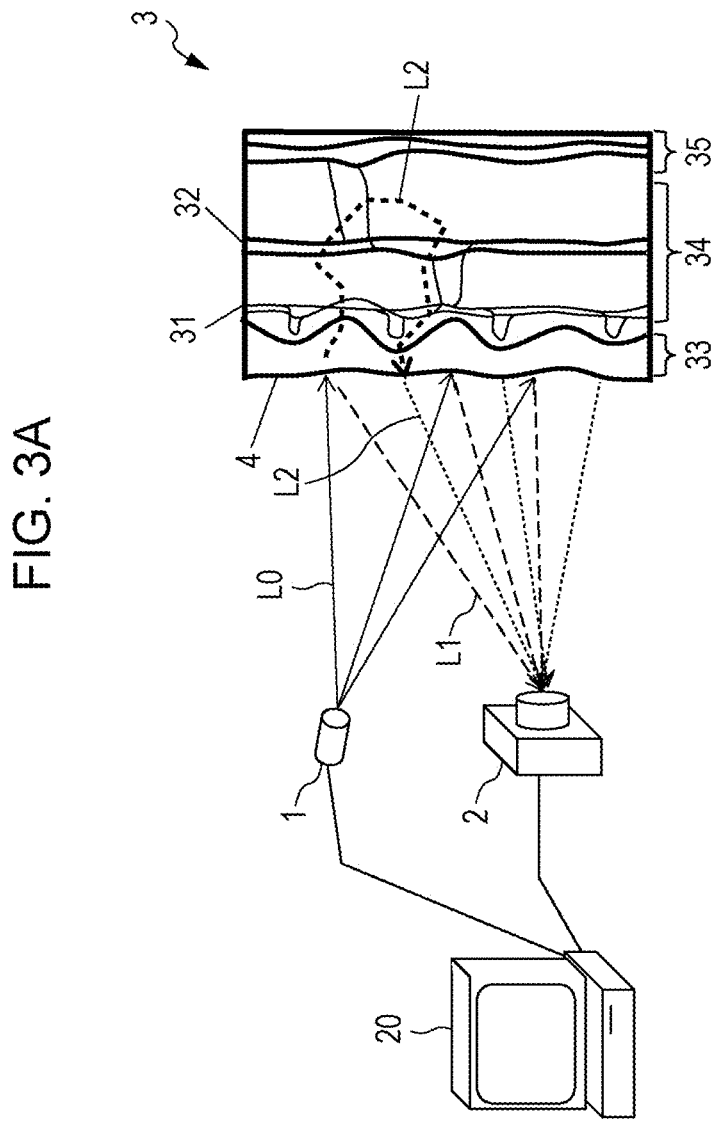
FIG. 3A is a diagram illustrating a configuration of a biological information detection device according to a first embodiment.

FIG. 3A is a diagram illustrating a schematic configuration of a human detection system according to the first embodiment. As illustrated in FIG. 3A, the human detection system according to the first embodiment includes a light source 1, an image capturing system (i.e., image capturing device or camera) 2, and a computer 20. The light source 1 is located at a position separate from a living body 3, for example, a human body and emits a light beam of a near-infrared wavelength range. The image capturing system 2 is capable of recording an image of a living-body surface 4 irradiated with light. The computer 20 separates and measures a component relating to directly reflected light reflected by the living-body surface 4 and a component relating to scattered light caused inside the body by using the captured image and calculates biological information on the basis of an intensity of the directly reflected light and an intensity of the scattered light, and outputs the resulting biological information.

The light source 1 is designed to project a dot pattern onto the living-body surface 4. Typically, a dot pattern is a collection of two-dimensionally arranged small bright points. A one-dimensionally arranged dot pattern may be used depending on the usage. In the first embodiment, for example, a random dot pattern laser projector RPP017ES available from Osela Inc. in Canada is used as the light source 1. This laser light source emits a near-infrared laser beam of 830 nm and projects a laser dot pattern including 57446 points in a 45°×45° viewing angle.

FIG. 3B is a diagram illustrating an example of a configuration of the image capturing system (hereinafter, also referred to as a camera) 2 and an example of a generated image. The camera 2 includes a lens 5 and a camera casing 6. The lens 5 may be a set of a plurality of lenses. The camera casing 6 includes therein an image sensor 7 and a bandpass filter 8 that passes only light of a wavelength of 830 nm±10 nm, which is the wavelength for the light source 1. The image sensor 7 has an imaging surface at which photodetector cells are disposed.

In the case where the subject is a person, the image sensor 7 obtains an image including a plurality of points each having a brightness corresponding to an infrared reflectance at a corresponding position, as illustrated at the center in FIG. 3B. An arithmetic circuit 22 included in the computer 20 is able to detect only a living body from this image by performing image signal processing, as illustrated on the right in FIG. 3B. As described before, a living body has a specific optical property called "optical tissue window" for a wavelength range of red to near-infrared light. Since human skin has a small absorption coefficient and a large scattering coefficient in this wavelength range, light that has transmitted through the skin surface, which is the living-body surface 4, repeats multiple scattering inside the body to scatter and then exits from a wide area of the living-body surface 4. The living body characteristically has a high proportion of scattered light relative to directly reflected light in the above wavelength range. In contrast, objects other than the living body has a high proportion of directly reflected light relative to scattered light. Accordingly, a living body can be detected based on the ratio between scattered light and directly reflected light.

Figure 3C:
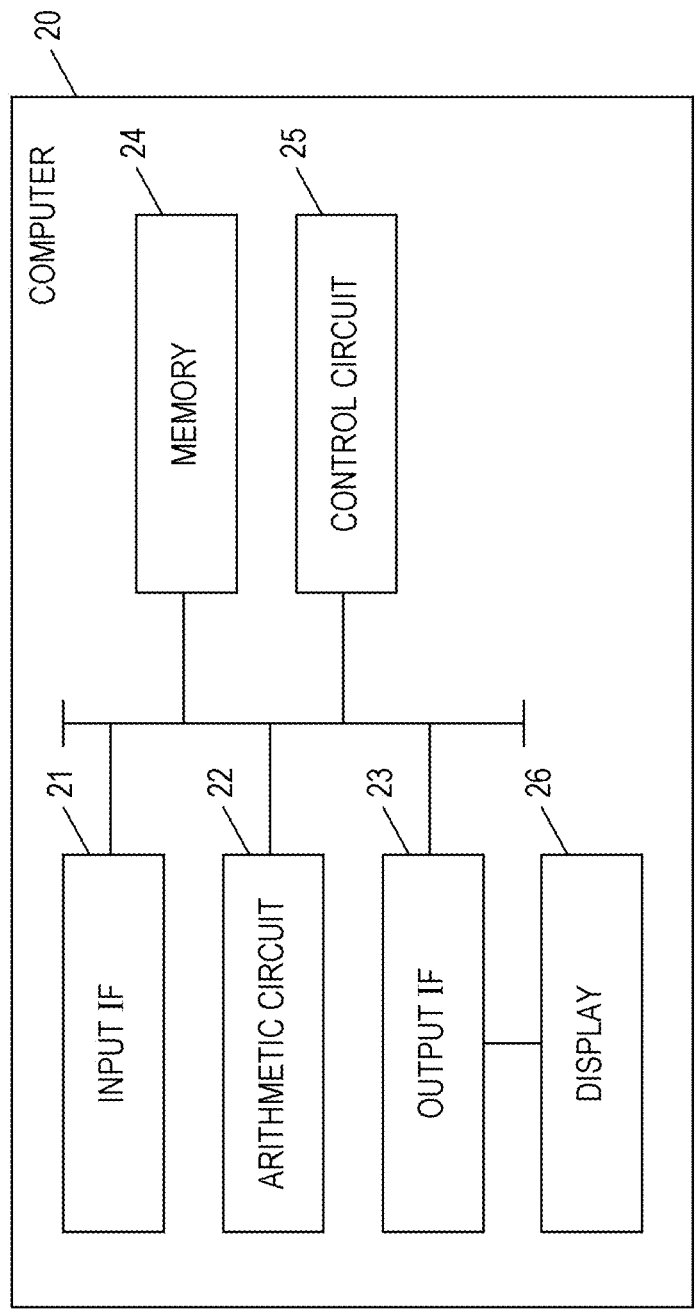
FIG. 3C is a block diagram illustrating a configuration of a computer in accordance with the first embodiment.

FIG. 3C is a block diagram illustrating a configuration of the computer 20. The computer 20 includes an input interface (IF) 21, the arithmetic circuit 22, a memory 24, a control circuit 25, an output interface (IF) 23, and a display 26. The input IF 21 is electrically connected to the camera 2. The arithmetic circuit 22 performs the aforementioned signal processing. The memory 24 stores various kinds of data. The control circuit 25 controls operations of the entire device. The output IF 23 outputs data. The display 26 displays a processing result. The arithmetic circuit 22 may be an image processing circuit, for example, a digital signal processor (DSP). The control circuit 25 may be an integrated circuit, for example, a central processing unit (CPU) or a microcomputer. The control circuit 25 runs a control program stored, for example, in the memory 24 to perform control, such as providing an instruction to switch on to the light source 1, an instruction to capture an image to the camera 2, and an instruction to perform computation to the arithmetic circuit 22. The control circuit 25 and the arithmetic circuit 22 may be implemented by a single circuit. In this example, the computer 20 includes the display 26; however, the display 26 may be an external device electrically connected to the computer 20 wirelessly or by a cable. The computer 20 may obtain, via a communication circuit (not illustrated), image information from the camera 2 located at a remote place.

An example of the human detection method that is carried out using actual data will be described below.

Figure 4A:
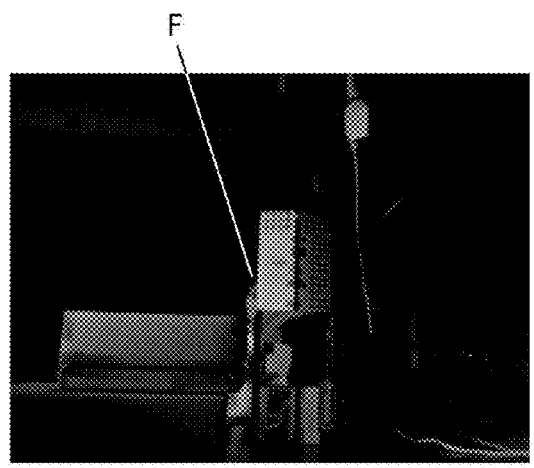
FIG. 4A is a diagram illustrating a first example to which a human detection method according to the first embodiment is applied.
Figure 4B:
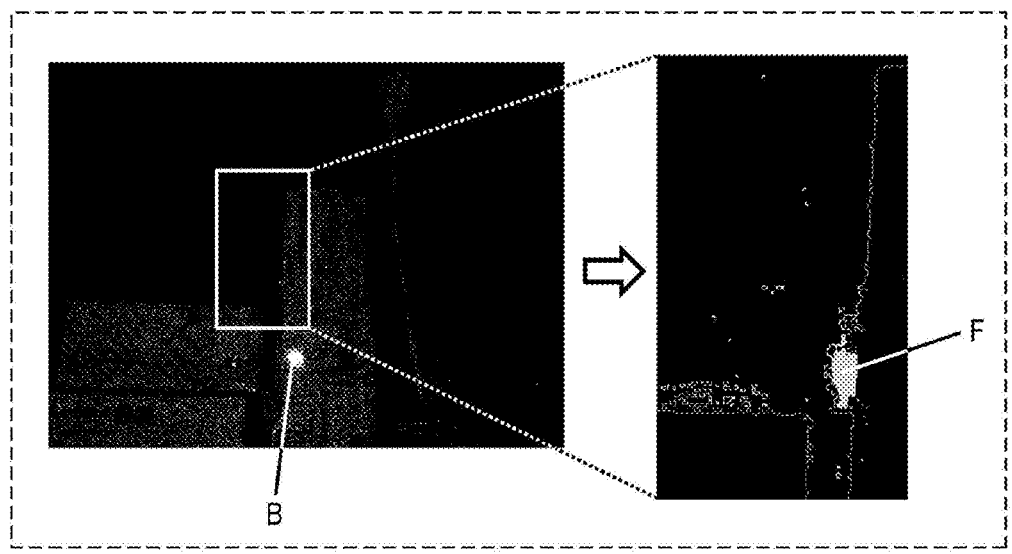
FIG. 4B is a diagram illustrating a second example to which the human detection method according to the first embodiment is applied.

FIG. 4A illustrates an example of an image obtained by an ordinary camera that detects visible light. The central part shows a face F of a person. An image on the left in FIG. 4B is an image that is obtained for the same scene as that of FIG. 4A by the camera 2 according to the first embodiment, with the place illuminated with the light source 1 of a wavelength of 830 nm. In this image, it is difficult to recognize the face F due to strong reflection by a box B located in the foreground. Accordingly, to detect a living body, the arithmetic circuit 22 calculates contrast of directly reflected light and scattered light from a near-infrared image.

Figure 5:
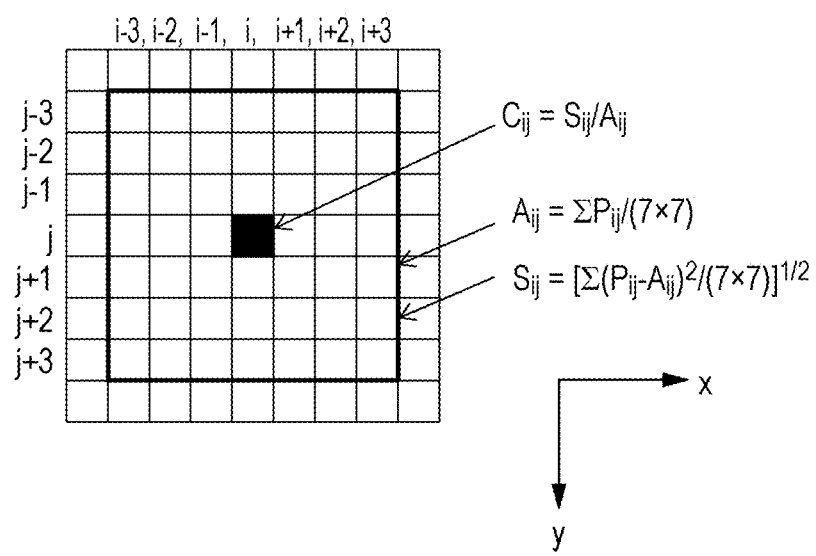
FIG. 5 is a diagram illustrating a contrast calculation method in accordance with the first embodiment.

FIG. 5 is a diagram illustrating an example of a pixel region used to calculate contrast. Image data is stored as two-dimensional intensity data in the memory 24. Here, Pij denotes data of a pixel located at an i-th column in the horizontal (x) direction and a j-th row in the vertical (y) direction. Contrast Cij for this pixel (i, j) is defined as follows:

$$Cij=Sij/Aij.$$

Here, Sij and Aij respectively denote a standard deviation and an average of pieces of data of pixels in a 7×7 pixel region centered at the pixel (i, j) and expressed by the corresponding equations illustrated in FIG. 5. Since the standard deviation Sij decreases as the ratio of scattered light to directly reflected light increases, the value of the contrast Cij decreases. After repeatedly performing this processing for all pixels, the arithmetic circuit 22 extracts only pixels for which the value of the contrast Cij is within a predetermined range. An example of an image that shows a part of a region where 0.2<Cij<0.47 is an image on the right in FIG. 4B. In this image, pixels for which the value of the contrast Cij is within the above range are shown in white, and the rest of the pixels are shown in black. The image indicates that a living body (i.e., the face F) is correctly extracted.

As described above, the arithmetic circuit 22 according to the first embodiment calculates the contrast Cij, which is a ratio between the standard deviation and the average of pixel values of a specific pixel included in an image and a plurality of pixels neighboring the specific pixel. Based on the value of the contrast Cij, the arithmetic circuit 22 is able to determine whether a living body is located at a position corresponding to the specific pixel and output information indicating the presence or absence of the living body.

According to the first embodiment, a living body hidden behind many objects can be efficiently detected by utilizing a specific optical property of a living body. The average and the standard deviation are derived for a 7×7 pixel region to derive a contrast of the image (i.e., contrast of directly reflected light and scattered light) in this example; however, this size of the pixel region is merely an example. The size (i.e., the number of pixels) of the pixel region used to compute the contrast may be appropriately set in accordance with the density of a plurality of dots formed by the light source 1 and the resolution of the camera 2. To suppress variance in the calculation result, a plurality of (e.g., three or more) dots may be included in a pixel region subjected to computation. The accuracy of the calculated contrast value improves by increasing the number of pixels included in the region subjected to computation; however, the resolution of the resulting image of the living body decreases. Accordingly, the number of pixels included in the region subjected to computation may be appropriately set in accordance with the configuration and usage of the system. Likewise, the predetermined contrast range is not limited to $0.2<Cij<0.47$ and is appropriately set in accordance with the configuration and usage of the system.

The system capable of detecting a living body in real time from a captured image as in the first embodiment is applicable to various usages. Typical usage examples will be described below.

(1) Finding Disaster Victims at Time of Disaster

Quickly finding disaster victims buried in rubble in response to occurrence of a natural disaster, such as earthquake, tsunami, or debris flow, is particularly important to save people's lives. There is "golden time of 72 hours", which indicates that the survival rate greatly decreases after 3 days passes, and it is necessary to quickly find disaster victims in chaos. The use of the system according to the first embodiment makes it possible to detect disaster victims hidden behind rubble in real time by capturing an image even in a circumstance where rubble is scattered everywhere. Since the system is small, the system can be installed on a drone, for example. This configuration makes it possible to capture an image while remotely controlling the system at a remote location and to search for survivors even if a disaster site is difficult to access because of a risk of a secondary disaster.

(2) Monitoring

Surveillance cameras are widely used and contribute to safe and secure daily life. As the number of surveillance cameras increases, it becomes more important how and who checks a video image captured by the surveillance cameras. Since it is difficult for a person to check the image all the time, the image is often used such that the image is accumulated and the image is checked after occurrence of a problem (crime) to grasp the situation. A utilization method may be adopted in which the moment at which a problem occurs is captured from a real-time image and the problem is immediately handled. The use of the technique according to the first embodiment of the present disclosure makes it possible to construct a system that recognizes a person when the person enters the field of view of a surveillance camera and warns a person in charge to prompt the person in charge to check the image in real time. A system can be constructed that frees the person in charge from the necessity of standing by in front of the monitor of the surveillance camera and that displays a warning and the image on a mobile terminal carried by the person in charge upon detecting a person. Such a system is suitable for monitoring at a backdoor of a warehouse or building where people rarely appear or a place where access is restricted. In addition, for a place, such as a building, where careful monitoring is performed with many surveillance cameras, highlighting a video image in which a certain person is detected may be useful to prevent an unusual situation from being overlooked or to find out an unusual situation at an early stage.

As for monitoring, development of a method in which a computer performs object recognition is in progress thanks to the advance in the image recognition technology, instead of a traditional method in which a person judges a monitoring image. For such a usage, a common method is that an image is transmitted to a host computer and the host computer performs recognition. However, since this method requires image data be transmitted to the host computer, this method involves issues such as an increasing amount of communications, a decreasing communication rate, and an increasing load of the host computer. If a surveillance camera is capable of performing preliminary recognition and judgement on an image, the load for communication, storage, and computation can be greatly reduced. However, if the recognition is not sufficiently reliable, the recognition may lead to overlooking of an event. Since a person can be highly reliably detected with the human detection method according to the first embodiment, only a partial image including a person can be selectively transmitted to the host computer upon detecting the person. Consequently, the surveillance system can be efficiently operated.

In addition, the progress in the image recognition technology makes it possible to identify an individual from an image at a high accuracy. In terms of identification of an individual from an image, a method in which an image is transmitted to a host computer and the host computer performs recognition is commonly used; however, this method also involves issues relating to load for communication, storage, and computation as described above. Specifically, an operation for extracting a face portion for face recognition imposes a heavy load during computation. The use of the human detection method according to the first embodiment allows the face portion to be easily extracted from an image. Accordingly, only the part of the image for the face portion can be transmitted to the host computer for individual identification, and the load for identifying an individual can be greatly reduced. Further, if the number of people to be identified is limited, a surveillance camera is able to immediately identify an individual without using the host computer by registering characteristics of the people in the surveillance camera in advance.

(3) Vehicles

Installation of the system according to the first embodiment in a vehicle makes it possible to recognize foot passengers on the street and implement safer driving. Even when a person is hidden behind an object and is scarcely seen, the system can detect the person and warn the driver. In terms of automated driving, in a situation where a vehicle cannot stop in response to breaking and an accident is inevitable even if the vehicle changes the direction to the left and to the right, a question about which direction the vehicle should head occurs. In such a case, it is effective to detect living bodies with the system according to the first embodiment and to change the heading direction to a direction in which the vehicle can avoid people. Since it is desired that the system quickly and highly accurately detect living bodies in such a usage, the system according to the first embodiment is particularly suitable.

(4) Switching based on Detection of Person

There is a wide variety of usages in which power is switched on and off by detecting a person. For example, there are usages in which switching of a device such as an air-conditioner or a light is controlled by detecting a person in a room, an automatic door is controlled at a high accuracy, a traffic light for foot passengers is controlled by detecting of a foot passenger at crossing, and brightness of an illumination of a vending machine is changed. The first embodiment is applicable to such usages. The use of the system according to the first embodiment can implement a sophisticated switch that does not respond to an object or pet but responds only to people. In such a usage, a small human detection sensor unit including the light source, the camera (image capturing system), and the signal processing device (arithmetic circuit) of the system according to the first embodiment may be constructed.

(5) Biometric Authentication

Biometric authentication, such as fingerprint authentication, iris authentication, and vein authentication, is widely used as a method for authenticating an individual. With the increasing use of such authentication, cases and a risk of spoofing in biometric authentication are increasing. An image duplication technology, such as copying, has been used in image-based authentication. Recently, with an increasing use of iris authentication and a three-dimensional printer, a risk of spoofing using a highly precise duplicate is increasing. As a countermeasure for such a risk, a two-step authentication system is effective. For example, a method is effective in which ordinary biometric authentication is performed after checking that a target is a living body using the human detection system according to the first embodiment. By checking that the target is a living body using the human detection system according to the first embodiment, the reliability of biometric authentication can be increased.

Second Embodiment

A system in which a technique of the present disclosure is applied to biological information sensing will be described as a second embodiment. With a growing interest in healthcare, importance of constant biological information sensing is increasing. A system capable of measuring biological information in a non-contact manner at all times is essential not only at hospitals but also for health management in daily life.

Figure 6B:
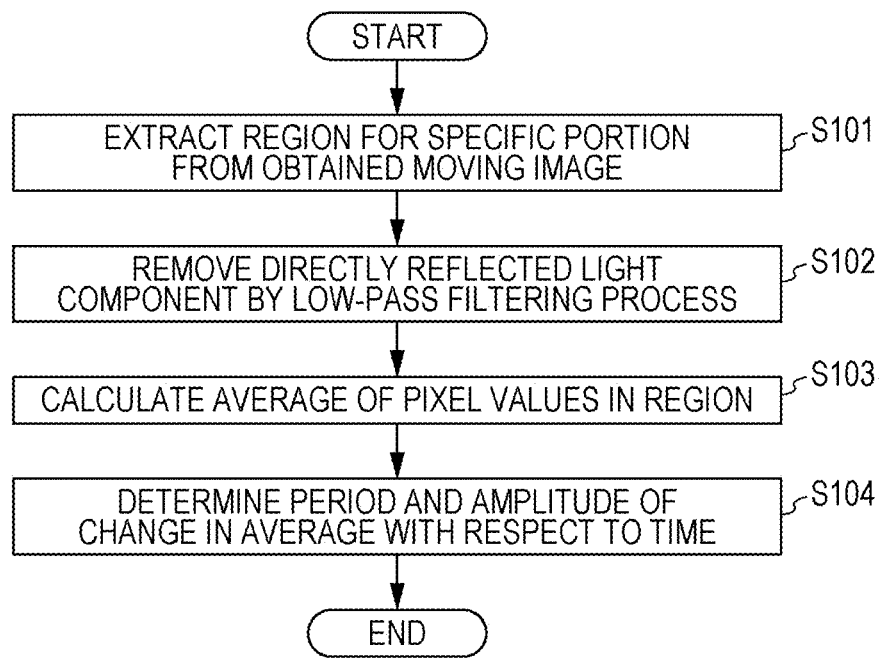
FIG. 6B is a flowchart illustrating a flow of an image processing process in accordance with the second embodiment.

The system according to the second embodiment is capable of monitoring heart rate and a fluctuation of heartbeat in a non-contact manner. The system has a physical configuration substantially the same as that of the first embodiment illustrated in FIG. 1. A difference from the first embodiment is a method of signal processing performed by the arithmetic circuit 22. Referring to FIGS. 6A and 6B, signal processing in accordance with the second embodiment will be described below.

FIG. 6A is a diagram illustrating an overview of signal processing in accordance with the second embodiment. FIG. 6B is a flowchart illustrating a flow of the signal processing. The arithmetic circuit 22 performs a known face recognition process on a video image obtained by the image sensor 7 and extracts a region for a specific portion (e.g., forehead portion) of the face (step S101). An image on the right end in FIG. 6A illustrates an example of values (pixel values) of pixels included in the extracted region. The arithmetic circuit 22 performs a two-dimensional lowpass filtering process on at least part of data (i.e., image signal) of the pixel values included in the region to remove a directly reflected light component (i.e., high-frequency component) (step S102). Then, the arithmetic circuit 22 calculates an average of the pixel values (i.e., reflected light intensities) in the region (step S103). The average of the reflected light intensities fluctuates over time as illustrated in a graph at a lower part of FIG. 6A. Since arterial blood ejected from the heart moves through a blood vessel while having a fluctuation called a pulse wave, an amount of absorbed near-infrared light changes with the pulse. Heart rate can be determined from a period of this fluctuation. Further, blood pressure or blood flow can be estimated from an amplitude of the pulse wave (step S104). As described above, the arithmetic circuit 22 is able to generate information concerning at least one of heart rate, blood pressure, and blood flow of a living body, on the basis of a change in a signal over time, the signal being obtained by performing a low-pass filtering process on at least part of an image signal.

It is known that mental stress can be estimated from a fluctuation of heart rate over time. It is known that a heartbeat interval fluctuates when the autonomic nervous system is functioning normally and that stress makes the fluctuation in heartbeat interval less frequent. The arithmetic circuit 22 according to the second embodiment is able to detect whether mental stress is imposed or how much stress is imposed, on the basis of a change in the fluctuation of heartbeat interval. To perform stress sensing in daily life at all times, a non-restraining and non-contact heartbeat sensing technique such as the second embodiment is essential.

Many methods for monitoring, with an ordinary visible light camera or a near-infrared camera, heartbeat in a non-contact manner have been proposed. Since separation of the surface reflected light component and the scattered light component is insufficient in these methods of the related art, non-contact measurement using such methods is easily influenced by disturbance light and stable and highly accurate measurement is difficult. Spatially separating the surface reflected light component and the scattered light component as in the second embodiment enables stable and highly accurate heartbeat measurement to be performed.

The use of the system according to the second embodiment makes it possible to monitor heart rate or blood pressure at all times including a period when the subject is sleeping, without restraining the subject. Consequently, a system can be constructed which monitors the condition of a patient at a hospital all the time and issues a warning to a medical personnel when something is wrong with the patient. At home, for example, heart rate of a patient who has the sleep-apnea syndrome can be monitored at nighttime. Further, since stress sensing can be performed easily in daily life as described above, people can live a full life.

Third Embodiment

A system for measuring blood oxygen saturation in a non-contact manner will be described as a third embodiment. The main role of blood is to receive oxygen at lungs, carries oxygen to tissues, receives carbon dioxide from tissues, and carries carbon dioxide back to lungs. Approximately 15 g of hemoglobin is present in 100 ml of blood. Hemoglobin loaded with oxygen is called oxyhemoglobin ($HbO_2$), whereas hemoglobin not loaded with oxygen is called hemoglobin or deoxyhemoglobin (Hb). As illustrated in FIG. 2, oxyhemoglobin and deoxyhemoglobin have different light absorption properties. Oxyhemoglobin absorbs infrared light of wavelengths exceeding approximately 830 nm relatively well, whereas deoxyhemoglobin absorbs red light (e.g., a wavelength of 660 nm) relatively well. There is no difference between absorbance of oxyhemoglobin and absorbance of deoxyhemoglobin for near-infrared light of a wavelength of 830 nm. Accordingly, in the third embodiment, transmitting light of two wavelengths, that is, 660 nm and 830 nm, are measured. A ratio (oxygen saturation) between two types of hemoglobin can be determined from a ratio between transmitting light of infrared light and transmitting light of red light. Oxygen saturation is a value indicating how much hemoglobin in blood is loaded with oxygen. The oxygen saturation is defined by Equation below.

$$\text{Oxygen saturation} = C(HbO_2)/[(C(HbO_2)+C(Hb)] \times 100 \,(\%),$$

where C(Hb) denotes a deoxyhemoglobin concentration, and C(HbO$_2$) denotes an oxyhemoglobin concentration.

A living body includes a non-blood components that absorb light of a wavelength of red to near-infrared light; however, a fluctuation in light absorbance over time results mainly from hemoglobin in arterial blood. Accordingly, a blood oxygen saturation can be measured at a high accuracy, based on a fluctuation of absorbance. Arterial blood ejected from the heart moves through a blood vessel as a pulse wave, whereas venous blood does not have a pulse wave. Light radiating a living body transmits through the living body after being absorbed at each layer of the living body, such as arteries, veins, and non-blood tissues; however, thickness of such tissues other than arteries does not change over time. Accordingly, scattered light from the living body shows a change in intensity over time in response to a change in the thickness of an arterial blood layer due to the pulse. This change reflects a change in thickness of the arterial blood layer, and does not contain the influence of venous blood and tissues. Thus, by focusing only on the change in the scattered light component, information concerning arterial blood can be obtained. Also, heart rate can be determined by measuring a period of a change in the component over time.

Figure 7:
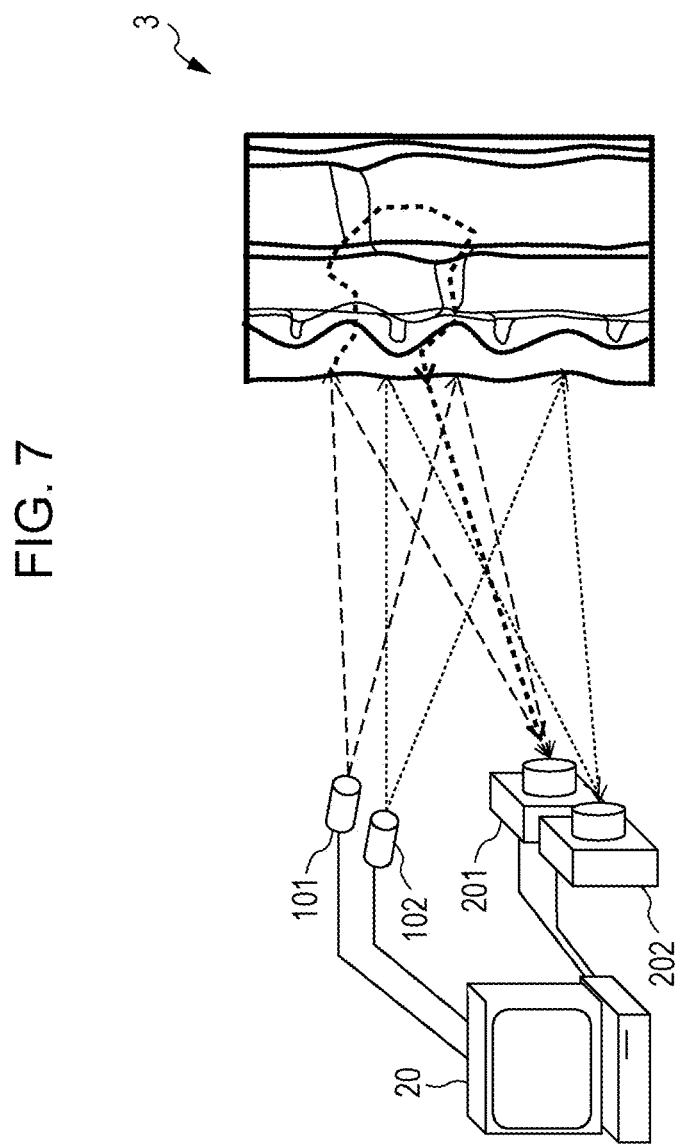
FIG. 7 is a diagram illustrating a configuration of a biological information detection device according to a third embodiment.

FIG. 7 is a diagram illustrating a configuration of the system according to the third embodiment. The system includes light sources 101 and 102, cameras 201 and 202, and a computer 20. The light sources 101 and 102 are two array point light sources that are disposed at positions separate from a living body 3 and emit a light beam of a wavelength of near-infrared light (e.g. wavelength of 830 nm) and a light beam of a wavelength of red light (e.g. wavelength of 660 nm), respectively. The cameras 201 and 202 are two image capturing systems capable of recording an image of a living-body surface 4 irradiated with light. The computer 20 separates and measures an intensity of directly reflected light reflected by the living-body surface 4 and an intensity of scattered light caused in the body from the obtained image and calculates biological information from the intensity of the directly reflected light and the intensity of the scattered light. In the third embodiment, the system includes the light sources 101 and 102, which are two array point light sources with different wavelengths, and the cameras 201 and 202 respectively corresponding to the light sources 101 and 102 in order to measure blood oxygen saturation.

Figure 8:
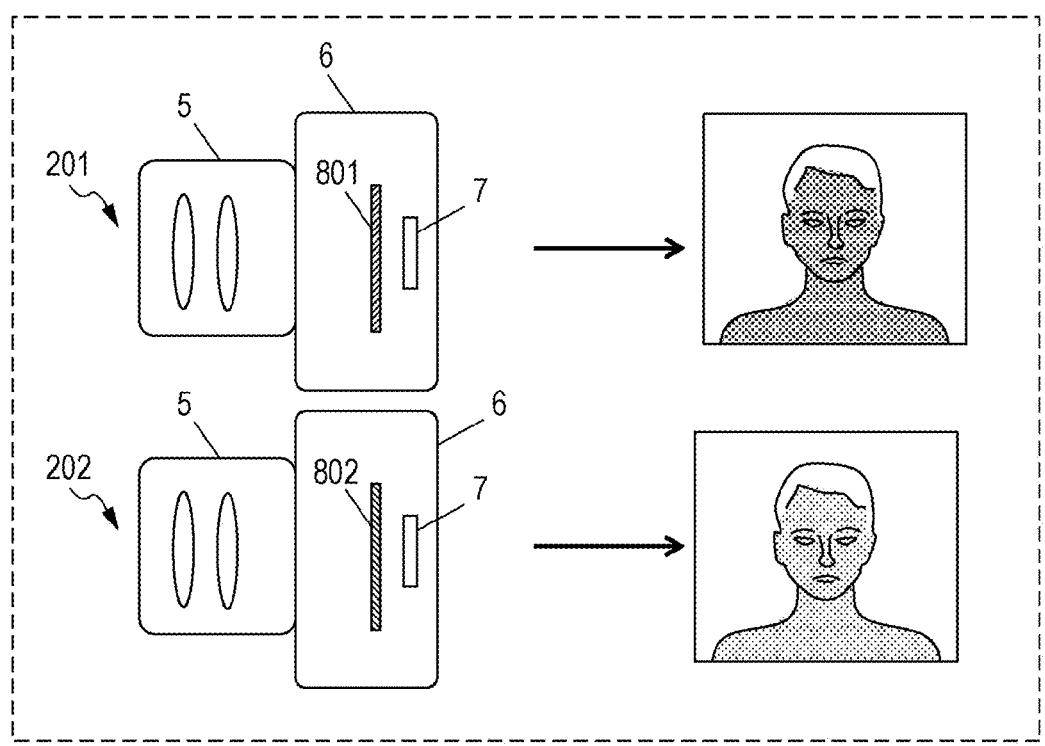
FIG. 8 is a diagram illustrating an overview of biological information sensing using two cameras in accordance with the third embodiment.

FIG. 8 is a diagram illustrating a configuration of the image capturing systems. Each of the cameras 201 and 202, which are the image capturing systems, includes a lens 5 and a camera casing 6. The camera casing 6 of the camera 201 includes therein an image sensor 7 and a bandpass filter 801 that selectively passes near-infrared light (wavelength of 830 nm). The camera casing 6 of the camera 202 includes therein the image sensor 7 and a bandpass filter 802 that selectively passes red light (wavelength of 660 nm).

For example, a random dot pattern laser projector RPP017ES available from Osela Inc. in Canada can be used as the light source 101. This laser light source is a 830-nm near-infrared laser light source and projects a laser dot pattern including 57446 points in a 45°×45° viewing angle. For example, a random dot pattern laser projector RPP016ES available from Osela Inc. in Canada can be used as the light source 102. This laser light source is a 660-nm red laser light source and projects a laser dot pattern including 23880 points in a 35°×35° viewing angle.

The computer 20 controls the cameras 201 and 202 and the light sources 101 and 102 so that the two cameras 201 and 202 operate together to simultaneously capture respective images. In this way, images based on light having two different wavelengths are generated by the cameras 201 and 202 as illustrated on the right in FIG. 8, for example.

Figure 9:
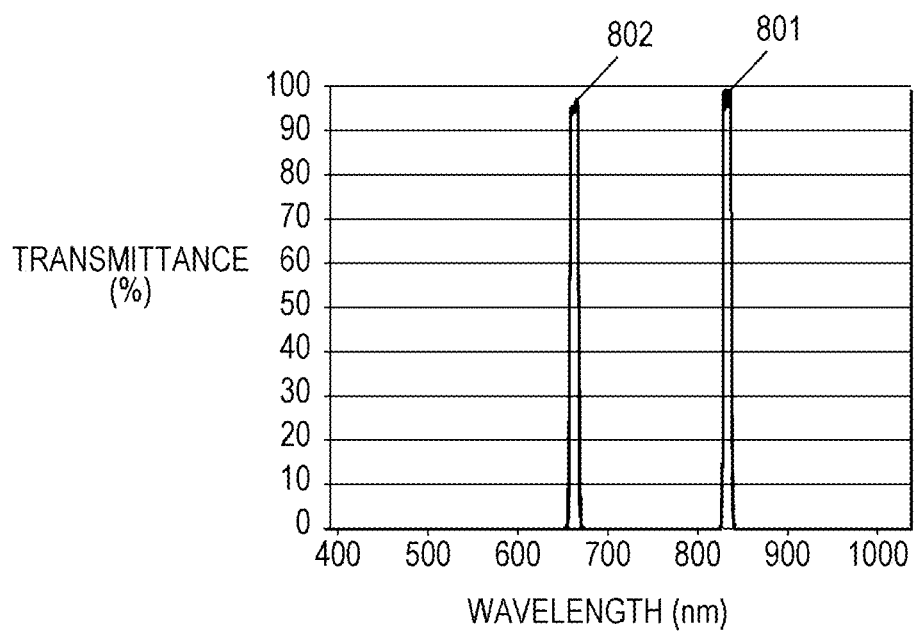
FIG. 9 is a diagram illustrating transmittance characteristics of two bandpass filters in accordance with the third embodiment.

FIG. 9 is a diagram illustrating transmittance characteristics of the bandpass filters 801 and 802. The bandpass filter 801 has a transmittance characteristic that the transmission center wavelength is 830 nm and the bandwidth is 10 nm. The bandpass filter 802 has a transmittance characteristic that the transmission center wavelength is 660 nm and the bandwidth is 10 nm. The transmission center wavelengths of the bandpass filters 801 and 802 respectively match central values of wavelengths of the light sources 101 and 102. Accordingly, the camera 201, which is the image capturing system, obtains an image based on light of a wavelength of 830 nm, whereas the camera 202, which is the image capturing system, obtains an image based on light of a wavelength of 660 nm.

The arithmetic circuit 22 of the computer 20 first performs a known face recognition process on a video image and extracts a region for a specific portion (e.g., forehead portion) of the face, as in the second embodiment. The arithmetic circuit 22 then performs a two-dimensional lowpass filtering process on data of pixels in the region to remove a directly reflected light component. Then, the arithmetic circuit 22 calculates an average of pixel values of the pixels in the region. The arithmetic circuit 22 performs the above process for each of the camera 201 for 830 nm and the camera 202 for 660 nm. The averages thus obtained indicate intensities of scattered reflected light from the living body 3.

Figure 10:
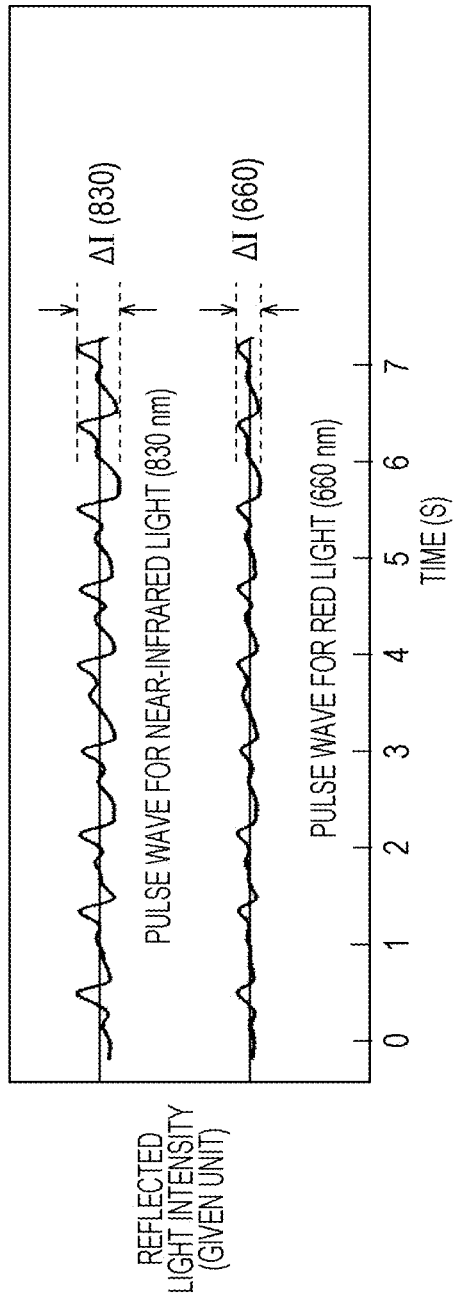
FIG. 10 is a diagram illustrating an example of pulse waves measured with a method according to the third embodiment.

FIG. 10 is a diagram illustrating an example of changes in the obtained scattered reflected light intensities over time. The reflected light intensity fluctuates over time for both near-infrared light (wavelength of 830 nm) and red light (wavelength of 660 nm). Here, let li(830) and li(660) respectively denote an intensity of light emitted from the light source 101 and an intensity of light emitted from the light source 102 at the living-body surface 4, and let Δl(830) and Δl(660) each denote an average of the fluctuation component of the scattered reflected light from the living body 3. Blood oxygen saturation SpO$_2$ is calculated using Equation below.

$$SpO_2 = a + b^*(\log(\Delta l(660)/\Delta l(660)))/(\log(\Delta l(830)/li(830))),$$

where a and b can be decided upon based on a relationship with measured values obtained by an existing pulse oximeter.

To check the accuracy of the measuring instrument, oxygen saturation at a fingertip instead of the forehead is measured using the system according to the third embodiment. Specifically, oxygen saturation at a fingertip is measured while blood flow is stopped by pressuring the forearm at a certain pressure (200 mmHg) using a belt (cuff) used to measure the blood pressure.

A commercially available pulse oximeter to which a finger is inserted is attached to the index finger. Oxygen saturation at the middle finger is measured in a non-contact manner using the system according to the third embodiment. The above values a and b are decided upon by the first measurement, and blood oxygen saturation SpO$_2$ is measured by the second and subsequent measurement.

Figure 11:
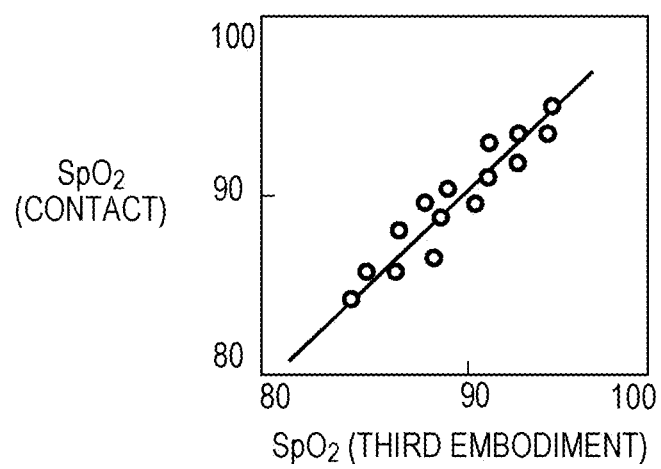
FIG. 11 is a diagram illustrating results obtained by measuring blood oxygen saturation with the method according to the third embodiment and a method of the related art.

FIG. 11 illustrates a comparison result of the measured values obtained using the pulse oximeter and measured values obtained in accordance with the third embodiment. Since both results substantially match, FIG. 11 indicates that measurement is performed accurately. In the method of the third embodiment, not only blood oxygen saturation but also heart rate can be simultaneously measured based on the pulse waves illustrated in FIG. 10.

It is known that stress and tiredness can be measured from the fluctuation or a frequency characteristic of the pulse wave. The use of the system according to the third embodiment makes it possible to estimate a mental condition, such as stress, and a physical condition of a subject from the pulse wave in a non-contact manner.

Fourth Embodiment

A method for measuring blood oxygen saturation by using one camera will be described as a fourth embodiment. In third embodiment, two cameras are used and signals for the light sources with different wavelengths are obtained by the respective cameras. This method has an advantage in that existing cameras can be used. However, since it is necessary to capture images by controlling two cameras to operate together, the configuration of the system becomes complicated. Also, since the obtained data is individual pieces of video data for the two cameras, synchronized data processing becomes complicated. To avoid such complexities, in the fourth embodiment, a camera capable of simultaneously obtaining data of images for two wavelengths is implemented.

Figure 12:
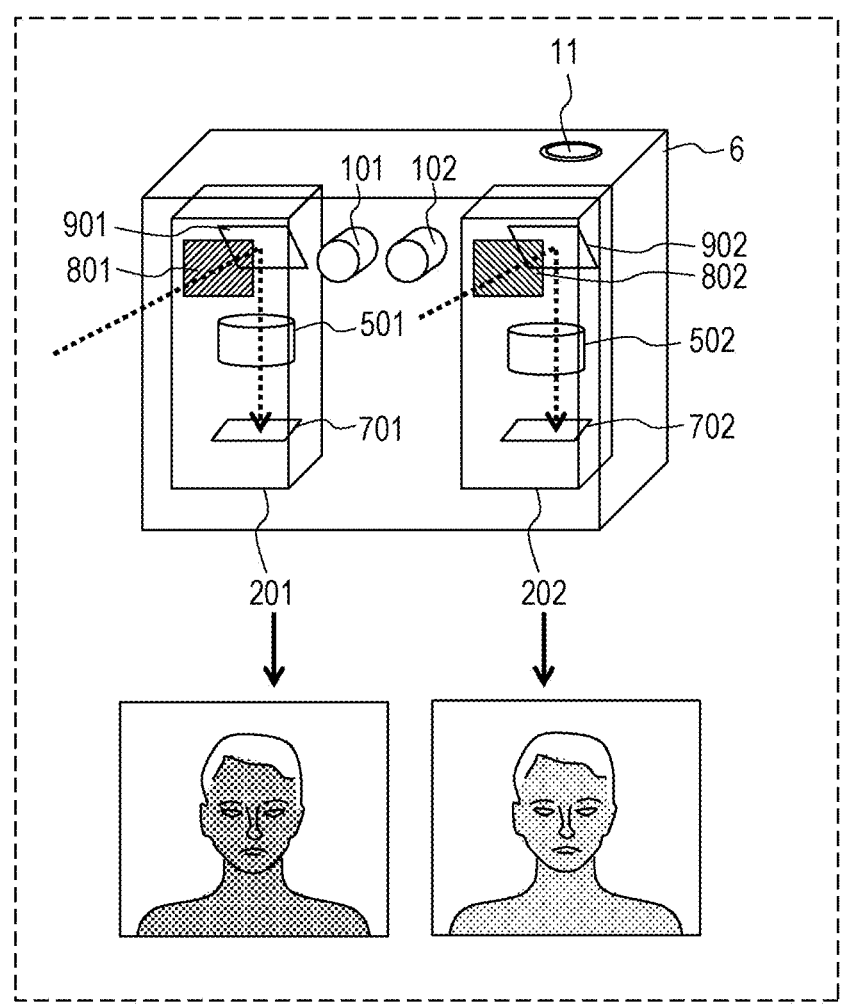
FIG. 12 is a diagram illustrating a configuration of a stereo-camera-type biological information detection device according to a fourth embodiment.

FIG. 12 is a diagram illustrating a configuration of a biological information detection device according to the fourth embodiment. This biological information detection device has a structure of a twin-lens reflex camera including two imaging optical systems 201 and 202. Accordingly, herein, such a configuration is referred to as a "stereo camera configuration". The biological information detection device (also referred to as a "camera") includes a light source 101 (wavelength of 830 nm), which is a first laser point light source, and a light source 102 (wavelength of 760 nm), which is a second laser point light source. The light emitted by the light sources 101 and 102 and reflected by a living body 3 respectively passes through bandpass filters 801 and 802. Then, the propagating direction of the light is bent by mirrors 901 and 902 by 90 degrees, and images are formed on imaging surfaces of image sensors 701 and 702 via lenses 501 and 502, respectively. The bandpass filters 801 and 802 are narrow-band bandpass filters that pass only light of a wavelength of 830±15 nm and light of a wavelength of 760±15 nm that correspond to wavelengths of the two light sources 101 and 102, respectively.

In response to pressing of a shutter button 11, the two light sources 101 and 102 switch on, and the image sensors 701 and 702 simultaneously obtain images of the living body 3. The obtained images are converted into images of a stereo-image format by an image processing processor (corresponding to the arithmetic circuit 22 in FIG. 3C), are subjected to image signal processing, and are accumulated in a storage device (corresponding to the memory 24 in FIG. 3C). The following processing is substantially the same as that of the second and third embodiments.

According to the fourth embodiment, by configuring an image capturing system as one stereo camera, the entire system becomes compact, and the configuration of the following signal processing system from image signal processing to calculation of oxygen saturation can be simplified. In this way, a simple and high-speed operation can be implemented.

For example, 760 nm and 830 nm, which are in a near-infrared range, can be used as wavelengths of the two light sources. Since a difference in absorbance between oxyhemoglobin and deoxyhemoglobin is larger for 660 nm used in the second and third embodiments than that for 760 nm, oxygen saturation can be measured more accurately for the wavelength of 660 nm. However, since the wavelength of 660 nm is in a visible light range, the use of this wavelength may impose a load on the subject. Further, since light of a fluorescent lamp and a light-emitting diode (LED) illumination contains a component of the wavelength of 660 nm, measurement is easily affected by ambient light. In the fourth embodiment, the wavelength of 760 nm is selected in consideration of such issues. Since a local absorbance peak of deoxyhemoglobin is at 760 nm, it is effective to use a wavelength of 760 nm to 780 nm if the wavelength of the light source having a shorter wavelength is set in the near-infrared range. The wavelengths used are not limited to the above ones, and may be appropriately selected in accordance with the usage and the use environment.

Fifth Embodiment

Another method for measuring blood oxygen saturation by using one camera will be described as a fifth embodiment. In the fourth embodiment, the stereo camera configuration in which one camera includes two optical systems and two image sensors is employed. In the fifth embodiment, a system is employed which obtains two different images corresponding to two wavelengths with one image sensor by dividing an image using a plurality of lenses. The configuration according to the fifth embodiment is referred to as a "stereo lens configuration". The system of the stereo lens configuration will be described with reference to FIG. 13.

Figure 13:
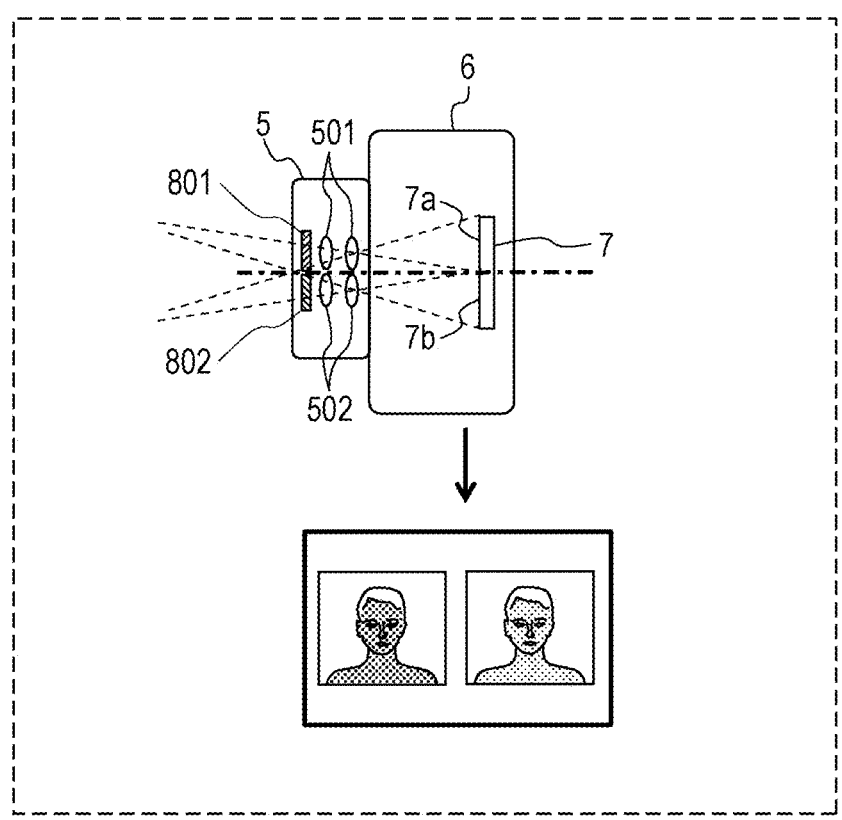
FIG. 13 is a diagram illustrating a configuration of a stereo-lens-type biological information detection device according to a fifth embodiment.

FIG. 13 is a cross-sectional view schematically illustrating a part of a biological information detection device according to the fifth embodiment. In the fifth embodiment, an imaging surface of an image sensor 7 includes a first region 7a in which first photodetector cells are disposed and a second region 7b in which second photodetector cells are disposed. Although not illustrated in FIG. 13, the biological information detection device includes, for example, in a camera casing 6, two light sources that project dot patterns formed by light of two wavelengths of 830 nm and 760 nm. As illustrated in FIG. 13, a lens 5, which is an optical system, includes therein two sets of lenses 501 and 502. The set of lenses 501 and the set of lenses 502, which are the optical systems, are designed to form respective images at the first region 7a and the second region 7b on the imaging surface of the image sensor 7, respectively. Two narrow-band bandpass filters 801 and 802 that pass light of 830 nm and 760 nm corresponding to the wavelengths of the two light sources are disposed in front of the sets of lenses 501 and 502, respectively. Specifically, the bandpass filter 801 is disposed on a path of light entering the first region 7a, whereas the bandpass filter 802 is disposed on a path of light entering the second region 7b.

With such a configuration, two images based on light of two wavelengths for the same time point can be obtained by using one image sensor 7. The arithmetic circuit 22 calculates blood oxygen saturation from the two images using the method similar to that of the second to fourth embodiments. According to the fifth embodiment, since one image signal include information concerning two images corresponding to two different wavelengths for the same time point, the arithmetic processing becomes easier.

A result obtained by performing stress sensing by using the system of this stereo lens configuration will be described below. As described above, a method for detecting, with thermography, a decrease in temperature at a nose portion due to stress (nervousness) or concentration has been proposed. The blood flow decreases at the nose portion due to a psychological change, and in response to the decrease in the blood flow, temperature decreases at the nose portion. A method for detecting such a temperature change with thermography is commonly performed. A change in temperature at the face is caused by a change in blood flow. If a change in blood flow can be measured at a high accuracy, stress sensing can be implemented that is more accurate and more responsive than in the case of measuring a change in the surface temperature, which occurs as a result of a change in blood flow.

Figure 14A:
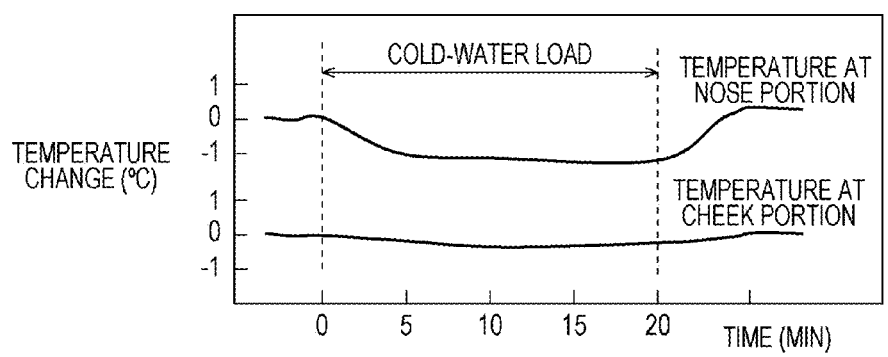
FIG. 14A is a diagram illustrating a result obtained by performing stress sensing using the biological information detection device according to the fifth embodiment.

FIG. 14A is a diagram illustrating a result of stress sensing performed using the biological information detection device according to the fifth embodiment. A cold-water load for immersing the right hand into cold water (ice water) is imposed as stress. For comparison, a temperature change is measured using thermography at a nose portion and a cheek portion enclosed by dotted lines in FIG. 14B. FIG. 14A illustrates results of this measurement. The temperature at the nose portion gradually decreases in about three minutes after the cold-water load is started to be imposed and becomes stable after decreasing by approximately 1.2° C. FIG. 14A indicates that temperature returns to the original level in about three minutes after the load is removed. In contrast, temperature at the cheek portion is hardly affected by the cold-water load and is stable.

Figure 14B:
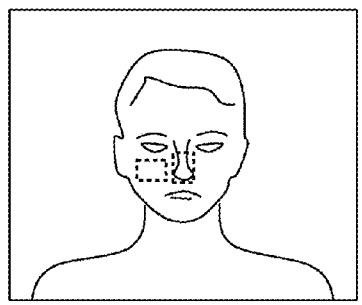
FIG. 14B is a diagram illustrating a nose portion and a cheek portion in an image in accordance with the fifth embodiment.
Figure 14C:
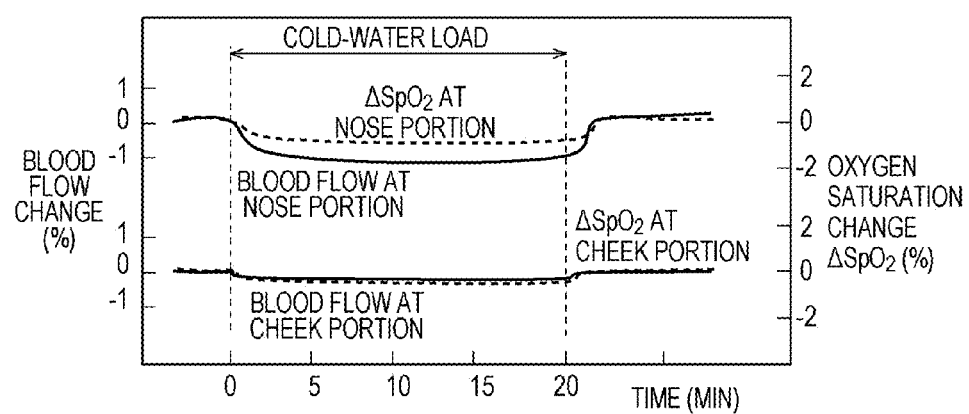
FIG. 14C is a diagram illustrating a change in blood flow and a change in blood oxygen saturation that are obtained using the biological information detection device according to the fifth embodiment.

FIG. 14C is a diagram illustrating a change in blood flow and a change in blood oxygen saturation that are obtained by the biological information detection device according to the fifth embodiment that employs the stereo lens configuration. Data for regions corresponding to the nose portion and the cheek portion, which are denoted by dotted-lines in FIG. 14B, are extracted from data of the blood flow and the oxygen saturation ($SpO_2$) at the face. A solid line denotes a change in the blood flow over time, whereas a dotted line denotes a change in the oxygen saturation ($\Delta SpO_2$) over time. As illustrated in FIG. 14C, the blood flow tends to decrease at the nose portion immediately after a cold stimulus is started, which indicates the responsivity with respect to time is high. In contrast, the blood flow hardly changes at the check portion. A decrease in the oxygen saturation is observed at the nose portion in response to a decrease in the blood flow, whereas the oxygen saturation hardly changes at the cheek portion.

As is apparent from the results, many pieces of data can be obtained by measuring blood flow and oxygen saturation at different portions of the face. An emotion, a physical condition, and a concentration degree can be detected at a high accuracy based on these pieces of data. The change in blood flow due to influence of the autonomic nervous system differs from portion to portion of the face. Thus, it is especially important to measure a change in blood flow at a specific portion by using the camera. At that time, the accuracy of the measurement can be increased by performing, at the same time, measurement at a portion where blood flow hardly changes and using the result as a reference.

Sixth Embodiment

Another method for measuring blood oxygen saturation by using one camera will be described as a sixth embodiment.

Figure 15:
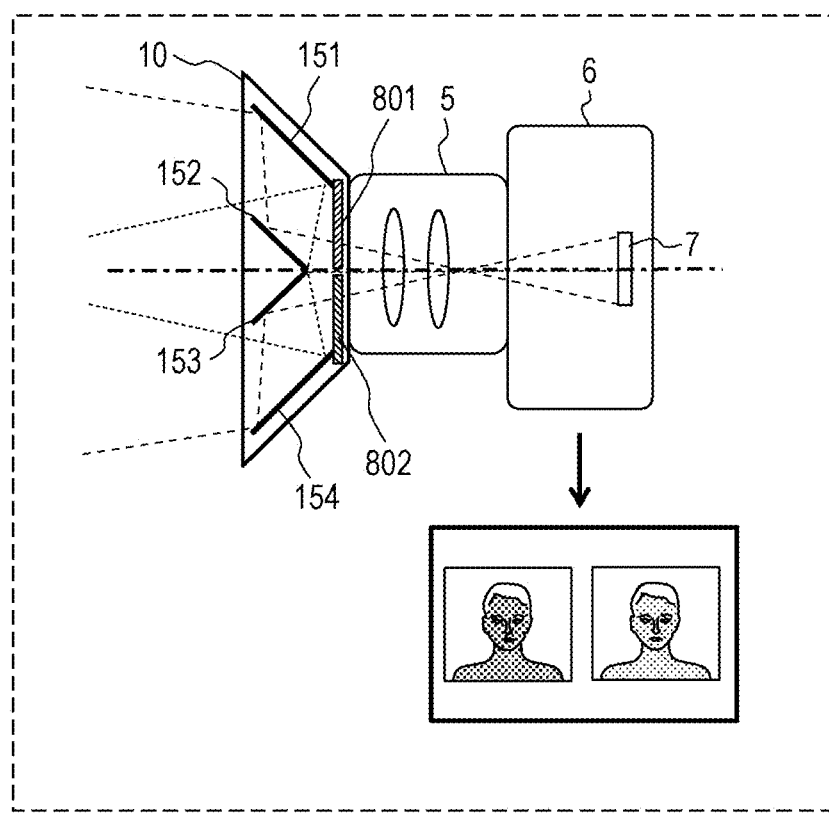
FIG. 15 is a cross-sectional view schematically illustrating a configuration of a biological information detection device according to a sixth embodiment.

FIG. 15 is a sectional view schematically illustrating a configuration of a biological information detection device according to the sixth embodiment. The biological information detection device includes a stereo adapter 10 attachable to an ordinary lens 5. The stereo adapter 10 is an attachment including four mirrors 151, 152, 153, and 154 and two bandpass filters 801 and 802. The use of the stereo adapter 10 allows two images corresponding to two wavelengths to be formed at two different regions of an imaging surface of an image sensor 7. This configuration is referred to as a "stereo adapter configuration".

In the stereo adapter configuration, two different images corresponding to two wavelengths can be obtained by one image sensor 7 by using two sets of facing mirrors. Although not illustrated in FIG. 15, two light sources that respectively emit light of two wavelengths of 830 nm and 760 nm are included in a camera casing 6. The stereo adapter 10 is attached to an end of the lens 5 of the camera. The two sets of mirrors (a set of mirrors 151 and 152 and a set of mirrors 153 and 154) bend the light path twice to guide the light to the lens 5. The narrow-band bandpass filters 801 and 802 that respectively pass light of the wavelengths of 830 nm and 760 nm corresponding to the wavelengths of the light sources are disposed between the lens 5 and the mirrors 151, 152, 153, and 154.

This biological information detection device is able to obtain images of two wavelengths for the same time point by using one image sensor 7. The basic concept is the same as that of the fifth embedment. Since the stereo lens configuration can make the lens small, the entire system can be advantageously made small. In contrast, with the stereo adapter configuration, the entire system becomes larger but a powerful camera lens can be used and the resolution can be improved. Also, lenses of different magnifications and zoom lenses can be used. The stereo adapter configuration advantageously increases the degree of freedom of the system.

A study for detecting an emotion of a person by using the biological information detection device (i.e., camera) according to the sixth embodiment has been carried out. As described in the fifth embodiment, a feeling or emotion such as stress of a human can be stably detected based on blood flow. In response to a change in a feeling or emotion of a person, the autonomic nervous system becomes more active and blood flow on the skin surface changes. As a result of this change in blood flow, facial color changes. People detect an emotion and a physical condition of a target person from a subtle change in facial color without any difficulty. It is considered that a reason why a great doctor can diagnose a patient's physical condition and a cause of a diseases by just looking at the patient's face is that such a doctor can identify a physical change from the subtle change in color of the patient's face. In addition, it is said that, when a person who is good at reading the situation reads a feeling of a counterpart, a subtle change in facial color as well as a subtle change in facial expression play an important role. Further, to make a situation natural and real in fields showing remarkable progresses recently, such as game, animation, and computer graphics, studies for subtly changing the facial color of a human character are widely carried out. As is apparent from these examples, the facial color represents an emotion and a physical condition of a person, and an attempt to read a feeling by measuring the facial color has been studied (for example, Kuroda et al., "Analysis of facial color and skin temperature in emotional change and its synthesis of facial color", Human interface 1(1), pp. 15-20, 1999). However, such an attempt to directly measure an emotion from facial color is not suitable for practical use because stable measurement is difficult. This is because a change in facial color differs from person to person, and stable measurement is difficult since a change in facial color is subtle and is strongly influenced by disturbance light and a camera. A method for stably and highly accurately detecting an emotion by a measure other than measuring a change in facial color is desired.

It is known that facial color of a person is mainly decided by an amount of melanin contained in the skin surface (dermis) and concentrations of hemoglobin (oxyhemoglobin and deoxyhemoglobin) in blood. Since the amount of melanin does not fluctuate in a short time (changes due to a factor such as aging or tanning), a change in emotion can be stably measured by measuring blood flow. In the sixth embodiment, instead of measuring facial color, blood flow of oxyhemoglobin and deoxyhemoglobin that changes facial color is directly measured to detect a change in emotion. As described in the fifth embodiment, a change in blood flow differs from portion to portion of the face because an impact of the influence of the autonomic nervous system differs from portion to portion of the face. For example, the nose portion is easily influenced by the autonomic nervous system because lots of arteriovenous anastomosis is located at the nose portion, whereas the forehead portion is hardly influenced by a skin blood vessel contraction nerve. The arithmetic circuit 22 according to the sixth embodiment determines blood flows at a plurality of different portions by computation and compares the obtained blood flows with each other, thereby being able to detect a change in emotion at a high accuracy.

Figure 16A:
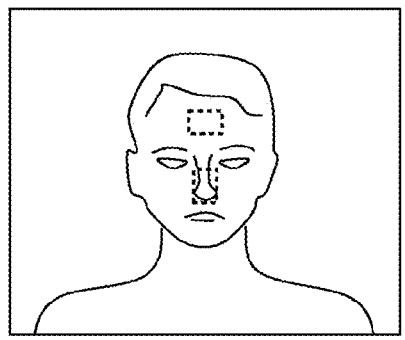
FIG. 16A is a diagram illustrating a nose portion and a forehead portion in an image in accordance with the sixth embodiment.

Measurement of a change in blood flow in response to an emotional change will be described below. The camera of the stereo adapter configuration illustrated in FIG. 15 is used to measure blood flow. A subject takes a seat in front of the camera, and an image of the subject's face is captured with the camera. Color images of the face of the subject are obtained while showing the subject a video image that induces, from the secured state, feelings such as fear, laughter, surprise, and disgust. An emotional change is read based on a change in scene in the video image and the facial change in the color images, and a change in blood flow at the time of such a change is measured. Blood flow is measured at the nose portion and the forehead portion as indicated by dotted lines in FIG. 16A.

Figure 16B:
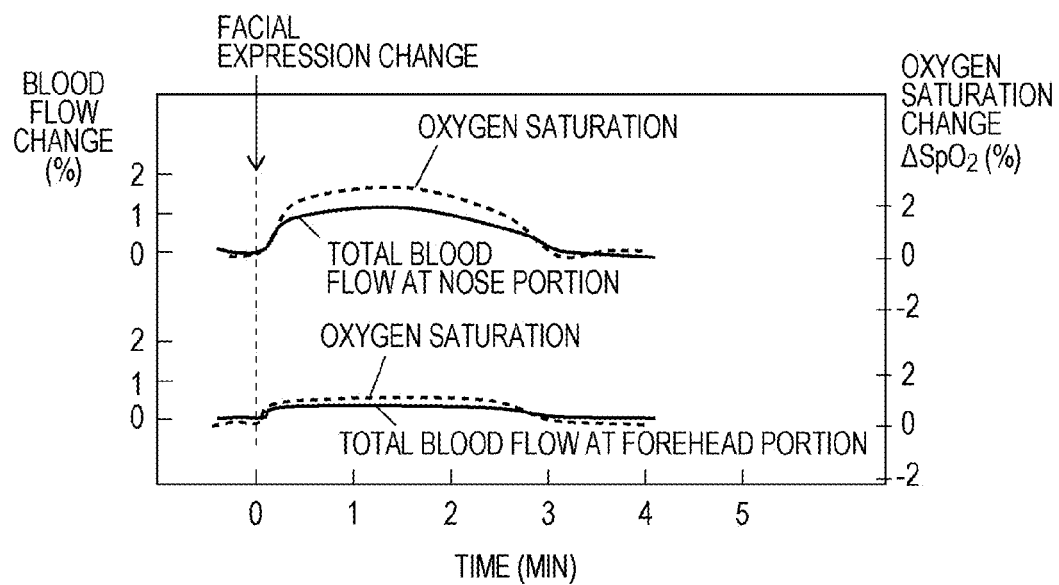
FIG. 16B is a diagram illustrating a change in total blood flow (oxyhemoglobin and deoxyhemoglobin) in time and a change in oxyhemoglobin blood flow (oxygen saturation) in time when an emotion causing laughter is induced in accordance with the sixth embodiment.

FIG. 16B is a diagram illustrating a change in total blood flow (oxyhemoglobin and deoxyhemoglobin) over time and a change in the percentage of oxyhemoglobin blood flow (oxygen saturation) over time when an emotion causing laughter is induced. FIG. 16B indicates that the value of the total blood flow and the value of the blood oxygen saturation greatly change in response to the emotional change causing laughter. Similar examinations are performed for other emotions. The total blood flow and an amount of change in the blood oxygen saturation are determined by calculation for the case where other emotions, such as sadness, surprise, depression, fear, disgust, anger, concentration, and happiness, are induced. The same measurement is performed for twelve subjects. Although there is a variation among individuals, the change in the total blood flow and the change in the blood oxygen saturation have showed the similar tendencies for almost all the subjects. This result indicates that an emotional change can be detected from at least one of blood flow and oxygen saturation.

As illustrated in FIG. 16B, a relationship between oxygen saturation and blood flow differs from portion to portion of the face. Accordingly, highly accurate emotion sensing can be performed by determining blood flow and oxygen saturation at a plurality of portions of the face. In the emotion sensing test performed in the sixth embodiment, measurement is performed at three portions, i.e., at the forehead, the cheek, and the nose. A change in oxygen saturation and a change in blood flow in response to an emotional change differ among the forehead, the cheek, and the nose. Accordingly, an emotional change can be detected highly accurately by creating in advance a table indicating a relationship between oxygen saturation and an amount of change in blood flow at each portion and calculating a correlation with the actually measured values of oxygen saturation and blood flow.

Seventh Embodiment

A method for measuring blood oxygen saturation by using one camera without dividing an image by an optical system will be described as a seventh embodiment. In the second to sixth embodiments, the method for dividing light from two light sources corresponding to two wavelengths, performing sensing, and determining biological information, such as oxygen saturation, by computation has been described. A biological information detection device according to the seventh embodiment obtains, with an image sensor, two image signals for different wavelengths without dividing an image.

Figure 17A:
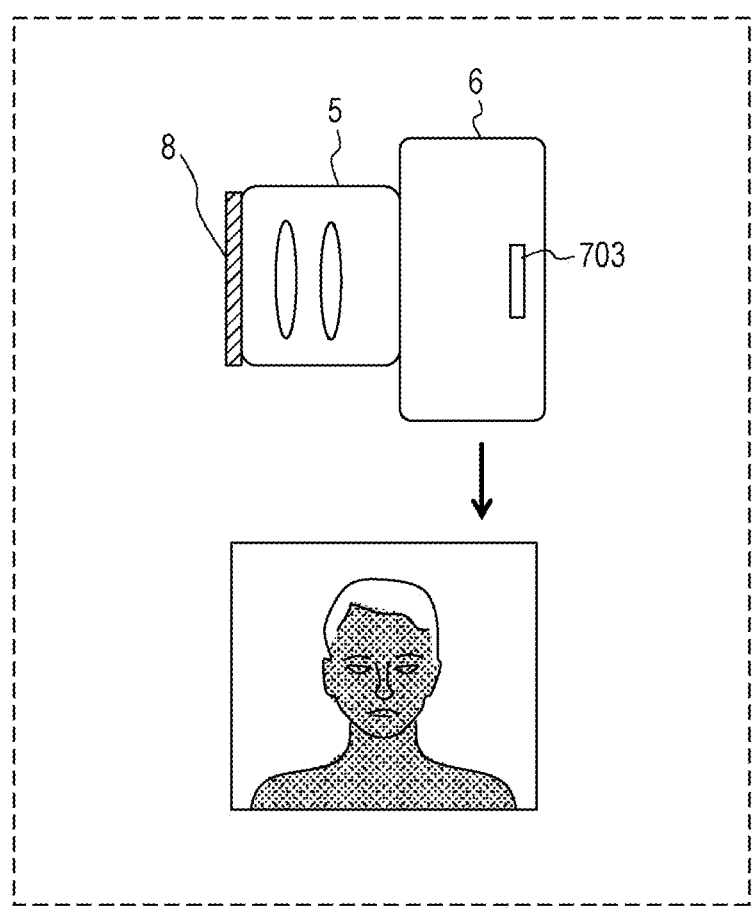
FIG. 17A is a diagram schematically illustrating a configuration of a biological information detection device according to a seventh embodiment.

FIG. 17A is a diagram schematically illustrating a configuration of the biological information detection device according to the seventh embodiment. This biological information detection device separate two images corresponding to two wavelengths not by the optical system but by an image sensor 703. Although illustration of point light sources is omitted in FIG. 17A, two light sources that respectively emit light of a wavelength of 830 nm and light of a wavelength of 760 nm are included in a camera casing 6. A bandpass filter 8 that passes light of a wavelength longer than or equal to 730 nm and shorter than or equal to 850 nm is disposed in front of a lens 5 of the camera. The bandpass filter 8 cuts visible light and infrared light of long wavelengths. Light that has passed the bandpass filter 8 forms an image on the imaging surface of the image sensor 703 via the lens 5. Unlike ordinary image sensors, the image sensor 703 used in the seventh embodiment includes two kinds of bandpass filters (hereinafter, also referred to as color filters) that pass near-infrared light.

Figure 17B:
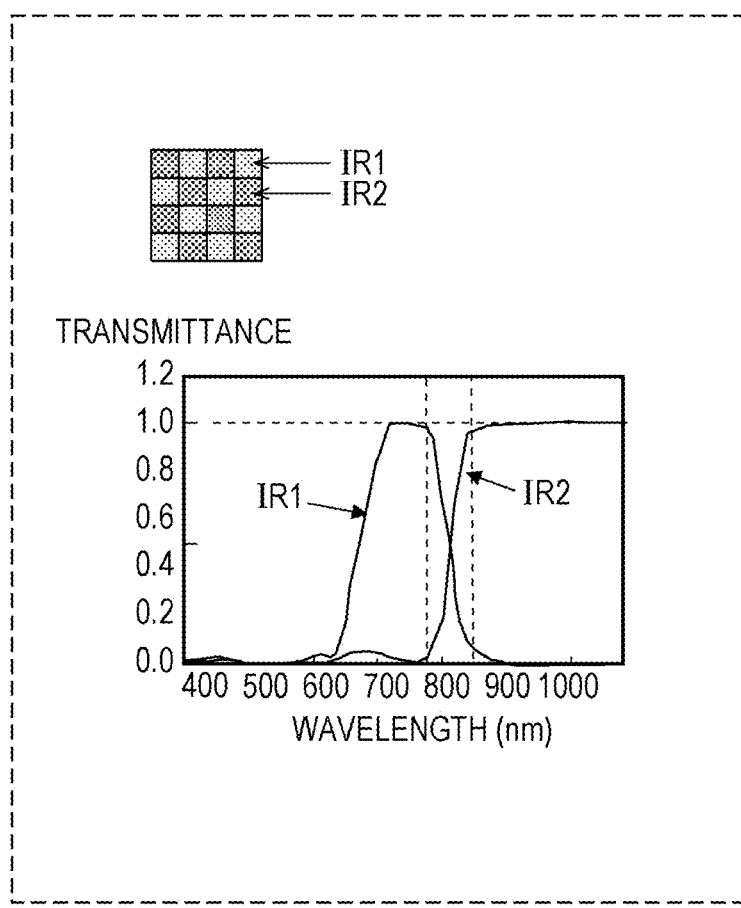
FIG. 17B is a diagram illustrating a plurality of color filters in accordance with the seventh embodiment.

FIG. 17B is a diagram illustrating a plurality of color filters that face a plurality of photodetector cells disposed on the imaging surface of the image sensor 703. The image sensor 703includes a plurality of color filters IR1 (also referred to as a first bandpass filter set) that selectively pass light of a wavelength of 680 nm to 800 nm and a plurality of color filters IR2 (also referred to as a second bandpass filter set) that selectively pass light of a wavelength of 800 nm or longer. The color filters IR1 and IR2 are arranged in a checkered pattern. The lower image in FIG. 17B is a diagram illustrating an example of wavelength dependency of transmittance of the color filters IR1 and IR2. The image sensor 703 detects, with a plurality of photodetector cells (also referred to as pixels), two images based on light of 760 nm and 830 nm which are wavelengths of the two light sources.

Figure 17C:
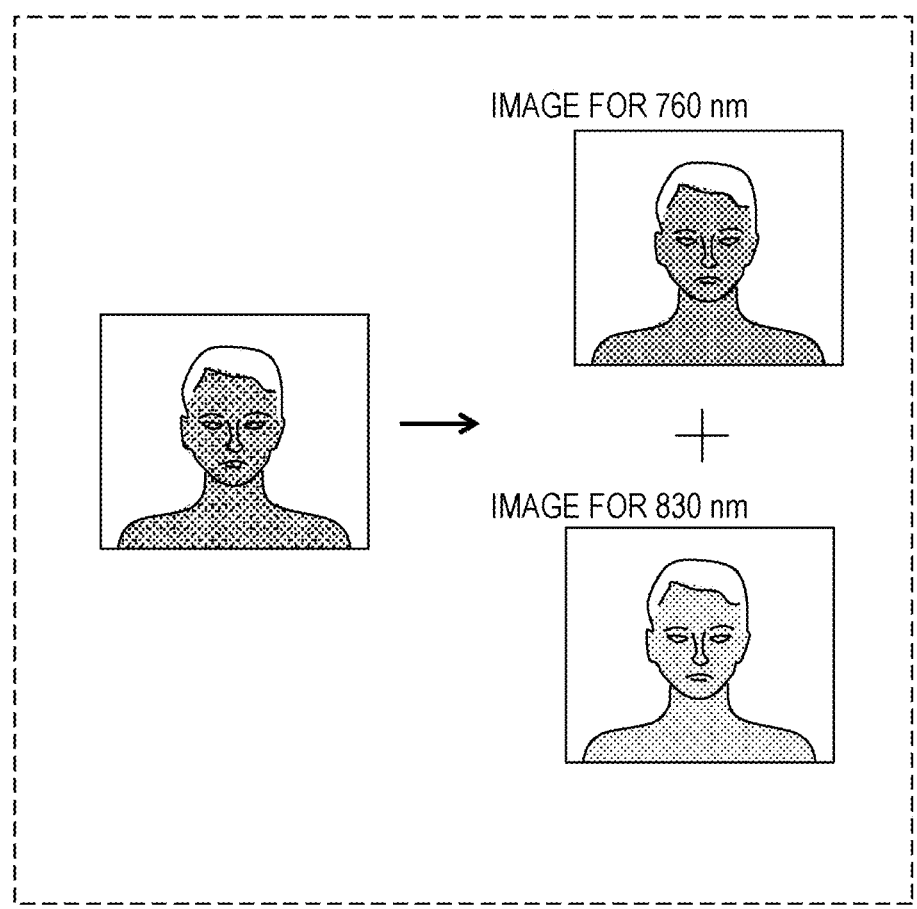
FIG. 17C is a diagram illustrating an example of images generated in accordance with the seventh embodiment.

The arithmetic circuit 22 (FIG. 3C) separately reads data obtained by the plurality of photodetector cells of the image sensor 703 for the wavelength of 760 nm and data obtained by the plurality of photodetector cells for the wavelength of 830 nm. As illustrated in FIG. 17C, the arithmetic circuit 22 generates an image for the wavelength of 760 nm and an image for the wavelength of 830 nm by adding, to the corresponding data, data for lacking pixels by interpolation. Since these two images completely coincide with each other, calculating blood flow and oxygen saturation from these images is easier than calculation using two different images. However, since the filtering performance of the filters is lower than that achieved in the case where bandpass filters corresponding to respective light sources are used, there is a concern about occurrence of color mixing between the light sources in this method.

Eighth Embodiment

A biological information detection device capable of obtaining not only two images corresponding light sources with two wavelengths without dividing an image but also a color image will be described as an eighth embodiment.

Figure 18A:
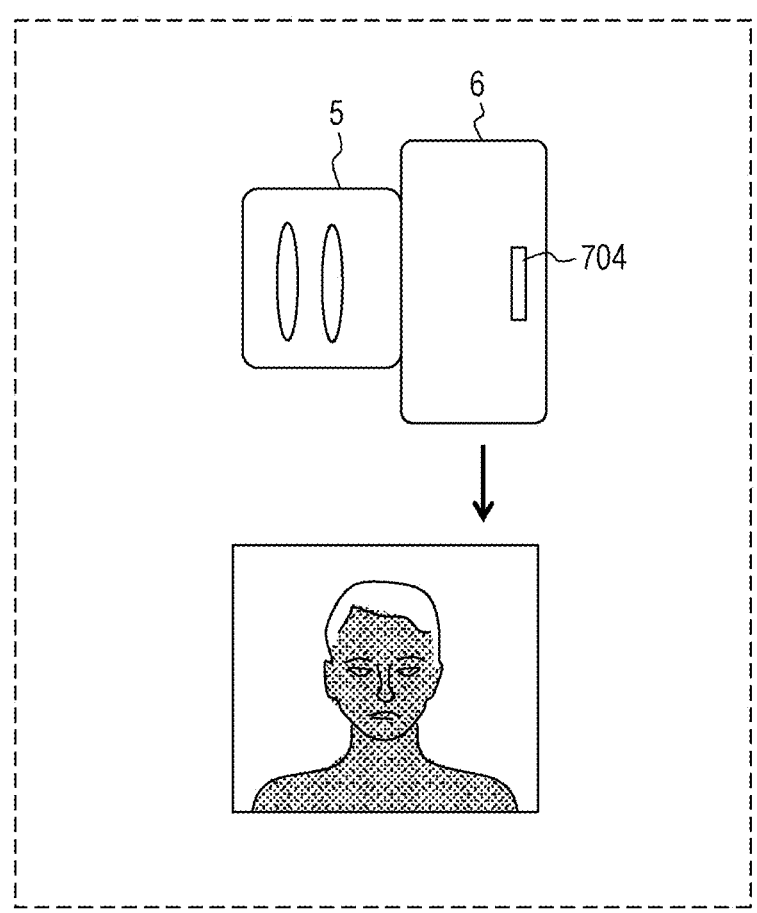
FIG. 18A is a diagram illustrating a configuration of a biological information detection device according to an eighth embodiment.

FIG. 18A is a diagram illustrating a configuration of the biological information detection device according to the eighth embodiment. Although illustration of point light sources is omitted also in FIG. 18, two light sources that respectively emit light of a wavelength of 830 nm and light of a wavelength of 760 nm are included in a camera casing 6. In the eighth embodiment, to obtain a color image, no bandpass filter is disposed in front of a lens 5. Visible light and light emitted by the leaser light sources form images on an imaging surface of an image sensor 704 via the lens 5. Unlike ordinary image sensors, the image sensor 704 used in the eighth embodiment includes photodetector cells that obtain a color image and two kinds of photodetector cells that obtain near-infrared images.

Figure 18B:
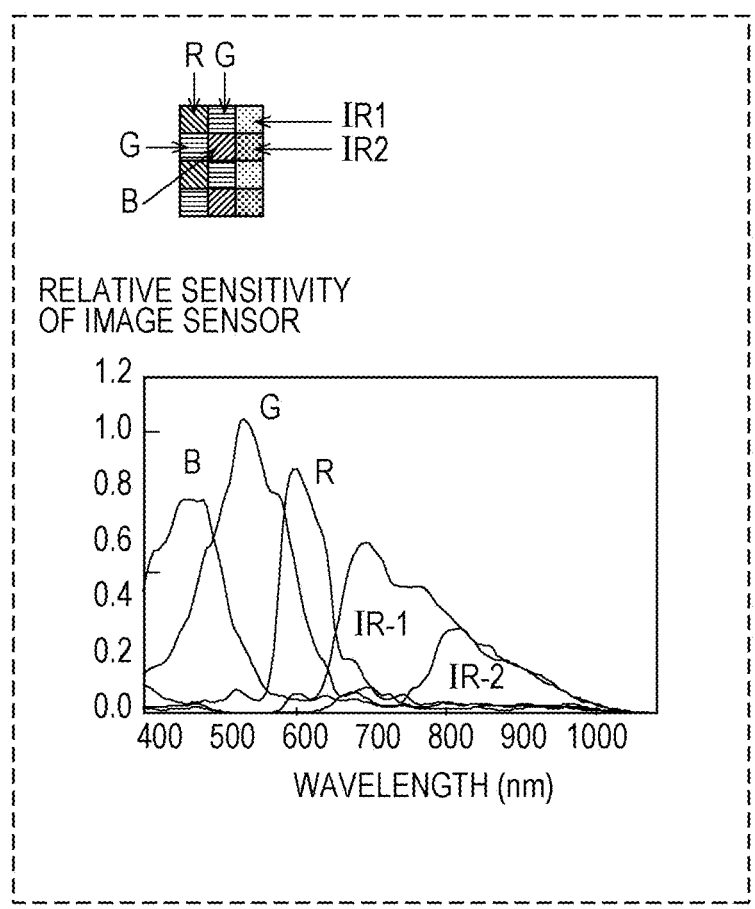
FIG. 18B is a diagram illustrating a plurality of color filters in accordance with the eighth embodiment.

FIG. 18B is a diagram illustrating a plurality of bandpass filters (or color filters) disposed on the imaging surface of the image sensor 704. The lower image in FIG. 18B illustrates wavelength dependencies of relative sensitivities of pixels that face corresponding filters. As illustrated in FIG. 18B, three types of color filters (R, G, and B filters) that respectively pass red light, green light, and blue light, filters IR-1 that pass light of 650 nm or longer, and filters IR-2 that pass light of 800 nm or longer are arranged on the imaging surface. The filters IR-1 are referred to as a first bandpass filter set. The filters IR-2 are referred to as a second bandpass filter set. R, G, and B filters are referred to as a third bandpass filter set. An array in which two G filters are disposed diagonally adjacent to each other and R and B filters are disposed on the opposite diagonal side is the same as the Bayer array of ordinary image sensors. This image sensor 704 differs from ordinary image sensors in that two filters IR-1 and IR-2 are arranged next to a basic unit of four filters arranged in the Bayer array.

Figure 18C:
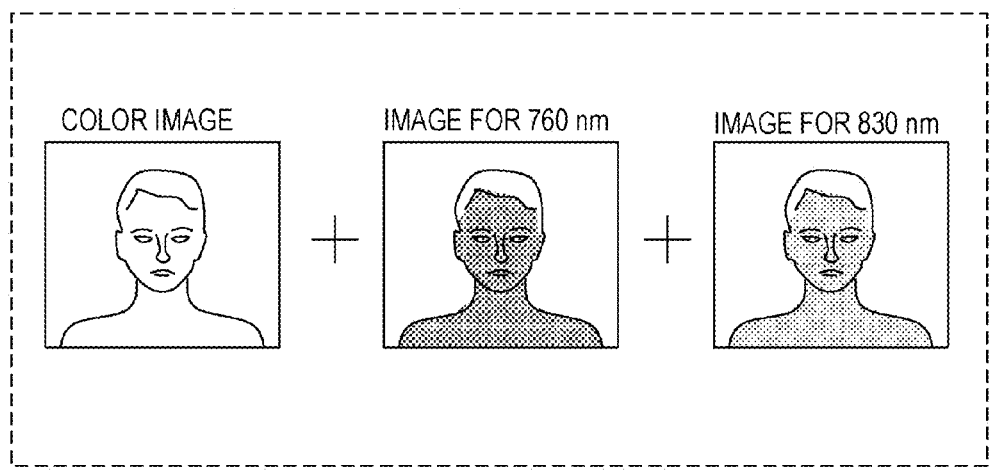
FIG. 18C is a diagram illustrating an example of images generated in accordance with the eighth embodiment.
Figure 18D:
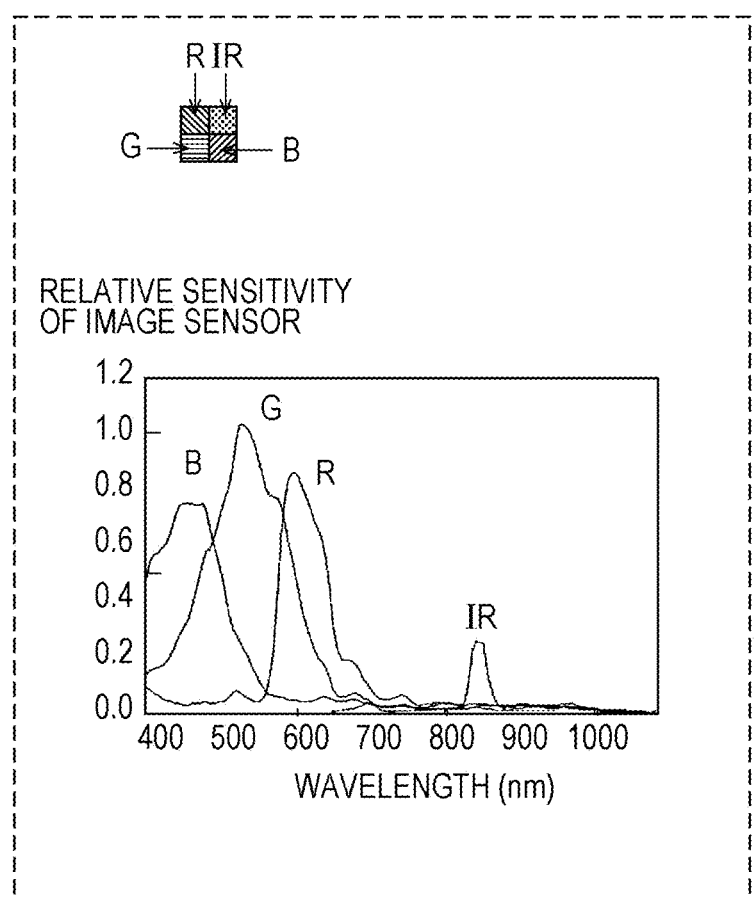
FIG. 18D is a diagram illustrating an example of a configuration of a multi-spectral sensor including four types of color filters of R, G, B, and IR.

The filter IR1 of the seventh embodiment and the filter IR-1 of the eighth embodiment have different transmission wavelength ranges. The filter IR1 of the seventh embodiment is a relatively narrow-band filter that passes light of a wavelength range from 650 nm to 800 nm. In contrast, in the eighth embodiment, a filter that pass light of a wavelength range of 650 nm or longer is used to simplify the manufacturing process of the image sensor 704. However, the configuration is not limited to this one, and the color filter described in the seventh embodiment can also be used. The filter IR-1 of the eighth embodiment is sensitive to both 760 nm and 830 nm. Accordingly, the arithmetic circuit 22 calculates a signal corresponding to 760 nm by subtracting the signal of the photodetector cells that face the filter IR-2 from the signal of the photodetector cells that face the filter IR-1 and then determines blood oxygen saturation. Consequently, an image (color image) of red, blue, and green, an image for the wavelength of 760 nm, and an image for the wavelength of 830 nm are determined by the image sensor 704 as illustrated in FIG. 18C.

In this configuration, color mixing is more likely to occur than in the seventh embodiment. However, a color image, blood flow, and blood oxygen saturation can be simultaneously obtained by the simple system using one camera.

In the eighth embodiment, an example of a configuration of a biological information sensing camera that uses a multi-spectral sensor that support five wavelengths including two wavelengths in an infrared range and three wavelengths (red, blue, and green) in a visible light range has been described. With the human-detection-type camera described in the first embodiment, capturing of a color image and human detection can be performed through measurement on four wavelengths including one wavelength in an infrared range and three wavelengths (red, blue, and green) in a visible light range. The multi-spectral sensor (illustrated in FIG. 18D, for example) having four types of color filters corresponding to four wavelengths is usable for such a purpose. A color filter is disposed such that a near-infrared (IR) pixel is assigned to one pixel out of two green pixels of the Bayer array that is commonly used in the image sensor. In the eighth embodiment, a camera for a system that switches on a near-infrared illumination of 850 nm is assumed, and a filter that selectively passes the wavelength of 850 nm is selected as a near-infrared filter. The use of such a camera makes it possible to use one camera system as an ordinary color camera and a human detection camera. Consequently, only one surveillance camera is needed, and it is easier to extract a color image of a portion in which a person is detected than in the case where two cameras are used. In the eighth embodiment, a color filter for 850 nm is used; however, the near-infrared filter may be changed in accordance with the near-infrared light source used.

Other Embodiments

While the embodiments of the present disclosure have been described above by way of example, the present disclosure is not limited to the above embodiments and can be variously modified. The process described in each of the above embodiments may be applied to other embodiments. Examples of the other embodiments will be described below.

In the embodiments above, laser light sources are used as the array point light sources; however, light sources of other types may be used. For example, less costly LED light sources may be used. However, light emitted by the LED light source has a lower straightness than that emitted by the laser light source and is more likely to spread. Accordingly, a dedicated condensing optical system needs to be used or some attention needs to be paid, such as restraining a distance between an image-capturing target and a camera. The number of array point light sources is not limited to one or two, and three or more light sources may be used.

The biological information detection device may include an adjustment mechanism that adjusts focus of the optical system. Such an adjustment mechanism can be implemented by, for example, a motor (not illustrated) and the control circuit 25 illustrated in FIG. 3C. Such an adjustment mechanism adjusts focus of the optical system to maximize contrast of a dot pattern image projected onto a target by the light source. With this configuration, accuracy of calculation of contrast described in the first embodiment improves.

The arithmetic circuit 22 may perform a face recognition process using image signals output by the image sensor and output information concerning a living body if the image includes at least one of a forehead, a nose, a mouth, an eyebrow, and hair. A system may be implemented that displays an error if none of the forehead, the nose, the mouth, the eyebrow, and the hair of a living body is included in the image.

The arithmetic circuit 22 may generate information concerning the epidermis including information concerning at least one of a melanin concentration, presence or absence of a spot, and presence or absence of a bruise on the basis of the image signal. As described above, the epidermis contains melanin that strongly absorbs light. A spot and a bruise are caused as a result of an increase in melanin. Accordingly, a melanin concentration, a spot, and a bruise can be detected based on an intensity distribution of light from the living-body surface.

In the present disclosure, the double camera configuration using two cameras (FIG. 7), the stereo camera configuration (FIG. 12) in which one camera includes two optical systems and two image sensors, the stereo lens configuration (FIG. 13) using two sets of lenses and one image sensor, the stereo adapter configuration (FIG. 15) using a lens adapter, one lens, and one image sensor, the configuration (FIG. 17A and FIG. 18A) that divides an image using the image sensor have been described. As already described, since each configuration has advantages and drawbacks, an appropriate configuration can be selected in accordance with the usage.

As described above, according to the embodiments of the present disclosure, not only heart rate and blood flow but also blood oxygen saturation can be measured without restraining a subject and without placing a detection device, such as a sensor, in contact with the subject. An emotion or a physical condition of the subject can also be estimated from measured values of blood flow and oxygen saturation at different portions of the subject.

What is claimed is:

1. A biological information detection device comprising:
   a first light source that, in operation, projects, onto a living body, at least one first dot formed by first light;
   a second light source that, in operation, projects, onto the living body, at least one second dot formed by second light;
   an image capturing system including
      first photodetector cells that, in operation, detect third light from the living body on which the at least one first dot is projected, and
      second photodetector cells that, in operation, detect fourth light from the living body on which the at least one second dot is projected,
   the image capturing system, in operation, generating and outputting a first image signal and a second image signal, the first image signal denoting a first image of the living body on which the at least one first dot is projected, the second image signal denoting a second image of the living body on which the at least one second dot is projected; and
   an arithmetic circuit that, in operation, generates information concerning the living body by using the first image signal and the second image signal output from the image capturing system and outputs the generated information, wherein:
   the first light includes fifth light having a wavelength longer than or equal to 650 nm and shorter than or equal to 950 nm;
   the second light includes sixth light having a wavelength longer than or equal to 650 nm and shorter than or equal to 950 nm; and
   the wavelength of the sixth light is longer than the wavelength of the fifth light by 50 nm or more.

2. The biological information detection device according to claim 1, wherein the image capturing system further includes
   an image sensor having an imaging surface divided into a first region in which the first photodetector cells are disposed and a second region in which the second photodetector cells are disposed,
   a first optical system that, in operation, forms the first image at the first region, and
   a second optical system that, in operation, forms the second image at the second region.

3. The biological information detection device according to claim 2, wherein the image capturing system further includes
   a first bandpass filter that is disposed on a path of the third light entering the first region and that, in operation, passes the third light, and
   a second bandpass filter that is disposed on a path of the fourth light entering the second region and that, in operation, passes the fourth light.

4. The biological information detection device according to claim 1, wherein the image capturing system further includes
   an image sensor
      having an imaging surface at which the first photodetector cells and the second photodetector cells are disposed, and
      including first bandpass filters that face the first photodetector cells and, in operation, pass the third light and second bandpass filters that face the second photodetector cells and, in operation, pass the fourth light, and
   an optical system that, in operation, forms the first image and the second image on the imaging surface.

5. The biological information detection device according to claim 1, wherein the image capturing system further includes
   an image sensor
      having an imaging surface at which the first photodetector cells, the second photodetector cells, and third photodetector cells are disposed, and
      including first bandpass filters that face the first photodetector cells and, in operation, pass the third light, second bandpass filters that face the second photodetector cells and, in operation, pass the fourth light, and third bandpass filters that face the third photodetector cells and, in operation, pass visible light, and
   an optical system that, in operation, forms the first image and the second image on the imaging surface, wherein:
   the third bandpass filters include color filters having different transmission wavelength ranges; and
   the image sensor, in operation, generates and outputs a color image signal by using the third photodetector cells.

6. The biological information detection device according to claim 1, wherein the arithmetic circuit, in operation, generates information indicating a blood oxygen saturation of the living body by using the first image signal and the second image signal and outputs the generated information.

7. The biological information detection device according to claim 1, wherein the arithmetic circuit, in operation,
   calculates, based on the first image signal and the second image signal, a blood flow and a blood oxygen saturation of the living body, generates, based on the blood flow and the blood oxygen saturation, information indicating at least one item selected from the group consisting of a physical condition, an emotion, and a concentration degree of the living body, and outputs the generated information.

8. The biological information detection device according to claim 1, wherein when the first image and the second image include at least one portion selected from the group consisting of a forehead portion and a nose portion of the living body, the arithmetic circuit, in operation, calculates, based on the first image signal and the second image signal, a blood flow and a blood oxygen saturation at the at least one portion selected from the group consisting of the forehead portion and the nose portion, generates, based on a change in the blood flow over time and a change in the blood oxygen saturation over time, information indicating at least one item selected from the group consisting of a physical condition, an emotion, and a concentration degree of the living body, and outputs the generated information.

9. The biological information detection device according to claim 1, wherein when the first image and the second image include a forehead portion and a nose portion of the living body, the arithmetic circuit, in operation, calculates, based on the first image signal and the second image signal, a blood flow and a blood oxygen saturation at the forehead portion and a blood flow and a blood oxygen saturation at the nose portion, generates, based on comparison of a change in the blood flow over time and a change in the blood oxygen saturation over time at the forehead portion with a change in the blood flow over time and a change in the blood oxygen saturation over time at the nose portion, information indicating at least one item selected from the group consisting of a physical condition, an emotion, and a concentration degree of the living body, and outputs the generated information.

10. The biological information detection device according to claim 1, wherein each of the first light source and the second light source is a laser light source.

11. The biological information detection device according to claim 1, wherein the image capturing system further includes an image sensor having an imaging surface at which the first photodetector cells and the second photodetector cells are disposed, an optical system that, in operation, forms the first image and the second image on the imaging surface, and an adjusting mechanism that, in operation, adjusts focus of the optical system, and wherein the adjusting mechanism adjusts the focus to maximize contrast of the first image and the second image.

12. The biological information detection method according to claim 1, wherein the arithmetic circuit, in operation, performs a face recognition process by using the first image signal and the second image signal, and generates the information concerning the living body in a case where the first image and the second image include at least one portion selected from the group consisting of a forehead, a nose, a mouth, an eyebrow, and hair of the living body.

13. The biological information detection device according to claim 1, wherein the information concerning the living body is information concerning at least one item selected from the group consisting of a melanin concentration, presence or absence of a spot, and presence or absence of a bruise.

* * * * *